United States Patent
Colman et al.

(10) Patent No.: US 10,314,515 B2
(45) Date of Patent: *Jun. 11, 2019

(54) CAPNOGRAPHY DEVICE AND METHOD

(71) Applicant: ORIDION MEDICAL 1987 LTD., Jerusalem (IL)

(72) Inventors: Joshua Lewis Colman, Jerusalem (IL); David Lain, Easton, MD (US); Boaz Giron, Jerusalem (IL)

(73) Assignee: Oridion Medical (1987) Ltd., Jerusalem (IL)

( * ) Notice: Subject to any disclaimer, the term of this patent is extended or adjusted under 35 U.S.C. 154(b) by 0 days.

This patent is subject to a terminal disclaimer.

(21) Appl. No.: 15/816,557

(22) Filed: Nov. 17, 2017

(65) Prior Publication Data

US 2018/0070859 A1 Mar. 15, 2018

Related U.S. Application Data

(63) Continuation of application No. 12/521,754, filed as application No. PCT/IL2008/000016 on Jan. 3, 2008, now Pat. No. 9,974,465.

(60) Provisional application No. 60/878,405, filed on Jan. 4, 2007.

(51) Int. Cl.
*A61B 5/08* (2006.01)
*A61B 5/083* (2006.01)
*A61B 5/00* (2006.01)

(52) U.S. Cl.
CPC ............ *A61B 5/0836* (2013.01); *A61B 5/082* (2013.01); *A61B 5/746* (2013.01); *A61B 5/08* (2013.01); *A61B 5/0816* (2013.01)

(58) Field of Classification Search
CPC ..... A61B 5/0836; A61B 5/0816; A61B 5/087; A61B 5/08; A61B 5/0803; A61B 5/082
See application file for complete search history.

(56) References Cited

U.S. PATENT DOCUMENTS

| | | | |
|---|---|---|---|
| 5,003,985 A * | 4/1991 | White | A61B 5/083 600/529 |
| 5,095,913 A | 3/1992 | Yelderman et al. | |
| 5,303,702 A | 4/1994 | Bonnet et al. | |
| 5,404,885 A | 4/1995 | Sheehan et al. | |
| 6,099,481 A | 8/2000 | Daniels et al. | |
| 6,342,039 B1 | 1/2002 | Lynn et al. | |
| 6,360,740 B1 | 3/2002 | Ward et al. | |

(Continued)

FOREIGN PATENT DOCUMENTS

| | | |
|---|---|---|
| WO | 9310844 A1 | 6/1993 |
| WO | 0118496 A1 | 3/2001 |

OTHER PUBLICATIONS

Imhoff M. et al., "Alarm Algorithms in critical care monitoring", Anesth Analg 102: 1525-1537 (2006).

(Continued)

*Primary Examiner* — Christian Jang
*Assistant Examiner* — Karen E Toth
(74) *Attorney, Agent, or Firm* — Fletcher Yoder PC

(57) ABSTRACT

There is provided a method for dynamically determining a breath related parameter, which includes averaging a breath related parameter over a first period of time, calculating a breath related value over a second period of time and adapting the duration of the first period of time according to the calculated breath related value.

20 Claims, 3 Drawing Sheets

(56) References Cited

U.S. PATENT DOCUMENTS

| | | | |
|---|---|---|---|
| 6,547,743 B2 | 4/2003 | Brydon | |
| 6,748,252 B2 | 6/2004 | Lynn et al. | |
| 9,974,465 B2* | 5/2018 | Colman | A61B 5/0836 |
| 2002/0173707 A1 | 11/2002 | Lynn | |
| 2003/0045806 A1 | 3/2003 | Brydon | |
| 2004/0006375 A1 | 1/2004 | Yann | |
| 2004/0187870 A1 | 9/2004 | Matthews et al. | |
| 2006/0155206 A1 | 7/2006 | Lynn | |
| 2007/0123792 A1* | 5/2007 | Kline | A61B 5/087 |
| | | | 600/538 |
| 2010/0036449 A1* | 2/2010 | Stalsberg | A61B 5/04525 |
| | | | 607/28 |
| 2010/0152600 A1 | 6/2010 | Droitcour et al. | |
| 2010/0249866 A1 | 9/2010 | Lovett | |
| 2011/0301427 A1 | 12/2011 | Fu et al. | |
| 2012/0150003 A1 | 6/2012 | Zhang | |
| 2013/0066198 A1 | 3/2013 | Grant et al. | |
| 2014/0180037 A1 | 6/2014 | Zhang | |

OTHER PUBLICATIONS

Takla G. et al., "The problem of artifacts in patient monitor data during surgery: A clinical and methodological review", Anesth Analg 103: 1196-1204 (2006).

European Supplemental Search Report of European patent application No. 08700250, dated Jan. 29, 2013.

International Search Report of PCT patent application No. PCT/IL08/00016, dated Aug. 25, 2008.

* cited by examiner

CAPNOGRAPHY DEVICE AND METHOD

CROSS-REFERENCE TO RELATED APPLICATIONS

This application is a continuation of U.S. Application Ser. No. 12/521,754, filed Mar. 31, 2010, which is the U.S. National Stage of International Application No. PCT/IL2008/000016, filed Jan. 3, 2008, which claims the benefit of U.S. Provisional Application No. 60/878,405, filed Jan. 4, 2007, the contents of each of which are herein expressly incorporated by reference in their entirety for all purposes.

BACKGROUND

Medical monitoring devices provide crucial data regarding a patient's medical condition. Two main types of monitors can be distinguished: those that monitor parameters that are a direct measure of one of the patient's physiological functions and those that monitor parameters that are an indirect measure of the status of a physiological function. An example of a parameter that is a direct measure of a physiological function is capnography, which measures and provides values of the $CO_2$ concentration in the ventilated breath, a direct measure of the patient's ventilation functioning. An example of a parameter that is an indirect measurement is blood pressure, which indirectly provides information regarding the functioning of the heart. In addition, some of the monitored parameters crucial for evaluating the patient's condition may be "rates" (for example, heart rate, breath rate) while others may be "snap shots", instantaneous type parameters (for example blood pressure, $CO_2$, $O_2$ concentrations).

Capnography is a non-invasive monitoring method used to continuously measure $CO_2$ concentration in exhaled breath. $CO_2$ is a constant metabolism product of the cells, and it is transported through the blood system to the lungs, from which it is eliminated through the alveolar membrane. The $CO_2$ is exhaled out of the body and the concentration of the exhaled $CO_2$, also known as end tidal $CO_2$ ($EtCO_2$) is an approximate estimation of the alveolar $CO_2$ pressure and thus of the arterial levels of $CO_2$. The measurements of the $CO_2$ concentration in a breath cycle are performed by a capnographer, and the results are a numerical value displayed also in a graphical format in the shape of a waveform named a capnogram. The numerical value of the results may be presented in units of pressure (mm Hg) or as a percentile. The capnogram may depict $CO_2$ concentration against total expired volume, but the more common capnogram illustrates $CO_2$ concentration against time.

Capnography is widely used today as an important tool for tracking a patient's ventilation status in various health care settings, such as in an Emergency Room (ER), Operation Room (OR), Intensive Care Unit (ICU) and Emergency Medical Services (EMS). Among the clinical applications in which capnography may be used are Cardiovascular (for example in CPR, shock, pulmonary embolism), Respiratory (for example, verification of endotracheal tubing, mechanically ventilated patients, conditions such as Asthma, hyperventilation, hypoventilation, apnea; Sedation (for example during operation); Patient transport (both intra- and inter-hospital), and the like.

Analyzing the capnogram may yield valuable information about the patient's clinical status. A normal capnogram exhibits one or more typical waveforms, each one represents a single respiratory cycle, and deviations from the normal waveform may hint as to the clinical situation of the patient. For example, an abnormally high basal line represents re-breathing of exhaled $CO_2$; a slow increase in $CO_2$ concentration may suggest uneven emptying of the lungs; a rise in $CO_2$ concentration without reaching a plateau may hint as to situations of asthma or other lower airway obstruction, very small changes in $CO_2$ concentration may indicate an apnea situation, and so forth.

In addition to displaying respiratory cycles, a trend display is also available in which many individual consecutive breath cycles are compressed together so that changes over time may be easily distinguished, providing yet an additional aid in assessing and monitoring the patient's ventilation and clinical profile.

An additional breathing related parameter useful in monitoring a patient's clinical status is the respiratory rate. Respiratory rate is defined as the number of breaths taken in a minute, and it may change under various physiological and medical conditions. The rate may be abnormally high (tachypnea), abnormally low (bradypnea) or non-existent (apnea).

To further assist the health care providers in monitoring the patient's clinical status, the medical monitoring device may set off an alert when deviations from the standard are detected. For example, a capnographer may set off an alert (an audio and or visible alarm) when deviations or changes in the patient's capnogram are detected, either in a single breathing cycle, or in the trend display. Likewise, when the respiratory rate deviates from normal, the monitor may set off an alarm, alerting the health care providers as to the change.

However, the assessment of issuing an alert by a medical monitoring device is complicated and includes many considerations for determining and balancing various parameters such as threshold limits, measurement time and rates in order to minimize false, non-clinically significant alerts (that result from artifacts) over genuine alerts (that result from authentic physiological change). Therefore, the need arises to develop such methods to improve the meaningfulness of the estimation of the measured parameter and hence the decision of issuing a clinically significant alert.

SUMMARY

The following embodiments and aspects thereof are described and illustrated in conjunction with systems, tools and methods which are meant to be exemplary and illustrative, not limiting in scope. In various embodiments, one or more of the above-described problems have been reduced or eliminated, while other embodiments are directed to other advantages or improvements.

According to some embodiments, there is provided a method for measuring a breath related parameter, the method including: measuring a breath related parameter (such as, for example, but not limited to, respiratory rate, $CO_2$ waveform patterns, $EtCO_2$, pulmonary index, and the like, or any combination thereof) over a first period of time, wherein the result of the measurement is averaged over the first period of time; obtaining a breath related value(s) over a second period of time, wherein the result is averaged over the second period of time; and wherein the first period of time and optionally the second period of time is (are) adapted to change according to the result of the measurement of the breath related parameter and/or the breath related value(s). The first and second periods of time may be periods of time that are determined by time units (such as, for example, number of seconds) or periods of time that are determined by number of occurrences of events, (such as, for example, number of breath cycles). The breath related value may then be used to dictate dynamically, in real-time the level of averaging and/or the time period used for calculating the average of the breath related parameter. The breath related value may indicate consistency and stable trends, or oppositely, indicate inconsistency, and thus may enable clinically significant conditions to be detected early, while non-clinically significant events may be lost within long averaging periods. There are, thus, further provided, methods for measuring and averaging the respiratory rate while reducing the number of non-clinically significant alarms. This may be performed by using an adaptive averaging time that may change in accordance with the status of stability of the patient. For example, the averaging time may be longer or shorter during instability or stability periods, respectively.

According to some embodiments, there is provided a method for dynamically determining a breath related parameter, which includes, averaging a breath related parameter over a first period of time, calculating a breath related value over a second period of time and adapting the duration of the first period of time according to the calculated breath related value. The method may further include adapting the duration of the second period of time according to the averaged breath related parameter, the calculated breath related value or both. The method may further include adapting the duration of the first period of time according to the averaged breath related parameter.

According to some embodiments, the breath related parameter may include respiratory rate, CO2 waveform, EtCO2, pulmonary index, or any combination thereof. The respiratory rate may be measured by number of breaths per minute (BPM). The breaths may be determined by the breath cycle.

According to some embodiments, the breath related value may include: variance of breath cycle periods, standard deviation of breath cycle periods, dispersion of breath cycle periods, average of breath cycle periods, ratio between inhalation and exhalation stages of breath cycle, respiration rate, CO2 waveform pattern, or any combination thereof.

According to some embodiments, the first period of time may be determined in time units, determined by number of occurrences of events or both. The events may include breath cycles.

According to some embodiments, the breath related parameter may be obtained by measuring, sampling, sensing, detecting, calculating, or any combination thereof.

According to some embodiments, the breath related value may be obtained by measuring, calculating, computing, detecting, deducing, or any combination thereof.

According to additional embodiments, the adapting may include shortening the duration of the first time period, extending the duration of the first time period, unchanging the duration of the first time period, or any combination thereof. The adapting may further include lowering the number of occurrences of events, increasing the number of occurrences of events, unchanging the number of occurrences of events, or any combination thereof.

According to some embodiments, there is provided a method for reducing non-clinically significant alarms produced by a medical monitoring device, the method includes: averaging a breath related parameter over a first period of time to obtain an averaged breath related parameter, calculating a breath related value over a second period of time to obtain a calculated breath related value, and adapting the duration of the first period of time according to the calculated breath related value.

According to additional embodiments, the method for reducing non-clinically significant alarms may further include averaging the breath related parameter over the adapted first period of time to obtain an updated averaged breath related parameter.

According to additional embodiments, the method for reducing non-clinically significant alarms may further include adapting the duration of the first period of time according to the averaged breath related parameter.

According to further embodiments, the method for reducing non-clinically significant alarms may further include setting off an alarm when the updated averaged breath related parameter is at or below a predetermined threshold. The method may further include setting off an alarm when the updated averaged breath related parameter is at or above a predetermined threshold.

According to some embodiments, the medical monitoring device may include a capnograph.

According to some embodiments the breath related parameter in the method for reducing non-clinically significant alarms may include: respiratory rate, CO2 waveform, EtCO2, pulmonary index, or any combination thereof. The respiratory rate may be measured by number of breaths per minute (BPM).

According to additional embodiments, the breath related value in the method for reducing non-clinically significant alarms may include: variance of breath cycle periods, standard deviation of breath cycle periods, dispersion of breath cycle periods, average of breath cycle periods, ratio between inhalation and exhalation stages of breath cycle, respiration rate, CO2 waveform pattern, or any combination thereof.

According to further embodiments, the first period of time in the method for reducing non-clinically significant alarms may be determined in time units, determined by number of occurrences of events or both. The second period of time is determined in time units, determined by number of occurrences of events or both. The events may include breath cycles.

According to some embodiments, the breath related parameter in the method for reducing non-clinically significant alarms may be obtained by measuring, sampling, sensing, detecting calculating, or any combination thereof. The breath related value may be obtained by measuring, calculating, computing, detecting, deducing, or any combination thereof.

According to some embodiments, adapting in the method for reducing non-clinically significant alarms may include shortening the duration of the first time period, extending the duration of the first time period, unchanging the duration of the first time period, or any combination thereof. Adapting may include lowering the number of occurrences of events, increasing the number of occurrences of events, unchanging the number of occurrences of events, or any combination thereof.

According to some embodiments, there is provided a device for dynamically determining a breath related parameter, the device includes: a processor adapted to average a breath related parameter sampled over the first period of time, wherein said processor is further adapted to calculate a breath related value over a second period of time and wherein said processor is further adapted to vary the duration of the first period of time according to the calculated averaged breath related value and to provide an updated averaged breath related parameter.

According to some embodiments, the device may further include a sampler adapted to sample the breath related parameter.

According to further embodiments, the device may further include an alarm unit adapted to set off an alarm when the updated averaged breath related parameter is at or below a predetermined threshold. The device may further include an alarm unit adapted to set off an alarm when the updated averaged breath related parameter is at or above a predetermined threshold.

According to some embodiments, the medical monitoring device may include a capnograph.

According to some embodiments, the medical monitoring device processor may be further adapted to vary the duration of the second period of time according to the averaged breath related parameter, the averaged calculated breath related value or both. The processor is further adapted to vary the duration of the first period of time according to the averaged breath related parameter.

According to further embodiments, the breath related parameter sampled by the device may include: respiratory rate, CO2 waveform, EtCO2, pulmonary index, or any combination thereof. The respiratory rate may be measured by number of breaths per minute (BPM) and the breaths may be determined by breath cycles. The breath related value may include: variance of breath cycle periods, standard deviation of breath cycle periods, dispersion of breath cycle periods, average of breath cycle periods, ratio between inhalation and exhalation stages of breath cycle, respiration rate, CO2 waveform pattern, or any combination thereof.

According to some embodiments, the first period of time may be determined in time units, determined by number of occurrences of events or both. The events may include breath cycles. The breath related value may be obtained by measuring, calculating, computing, detecting, deducing, or any combination thereof.

According to some embodiments, varying of the duration of time periods may include: shortening the duration of the first time period, extending the duration of the first time period, unchanging the duration of the first time period, or any combination thereof. Varying of the duration may further include lowering the number of occurrences of events, increasing the number of occurrences of events, unchanging the number of occurrences of events, or any combination thereof.

According to additional embodiments, there is provided a system for dynamically determining a breath related parameter, the system includes: a device that includes a processor adapted to average a breath related parameter sampled over the first period of time, wherein said processor is further adapted to calculate a breath related value over a second period of time and wherein said processor is further adapted to vary the duration of the first period of time according to the calculated breath related value and to provide an updated averaged breath related parameter.

According to some embodiments, the device in the system for dynamically determining a breath related parameter may include a capnograph. The device may further include a sampler adapted to sample the breath related parameter. The device may further include an alarm unit adapted to set off an alarm when the updated averaged breath related parameter is at or below a predetermined threshold. The alarm unit may be further adapted to set off an alarm when the updated averaged breath related parameter is at or above a predetermined threshold.

According to some embodiments, the device may further include one or more displays adapted to display the breath related parameter, the breath related value, the first period of time, the second period of time, or any combination thereof.

In addition to the exemplary aspects and embodiments described above, further aspects and embodiments will become apparent by reference to the figures and by study of the following detailed descriptions.

BRIEF DESCRIPTION OF THE FIGURES

Examples illustrative of embodiments are described below with reference to figures attached hereto. In the figures, identical structures, elements or parts that appear in more than one figure are generally labeled with a same numeral in all the figures in which they appear. Dimensions of components and features shown in the figures are generally chosen for convenience and clarity of presentation and are not necessarily shown to scale. The figures are listed below.

DETAILED DESCRIPTION

Figure 1:
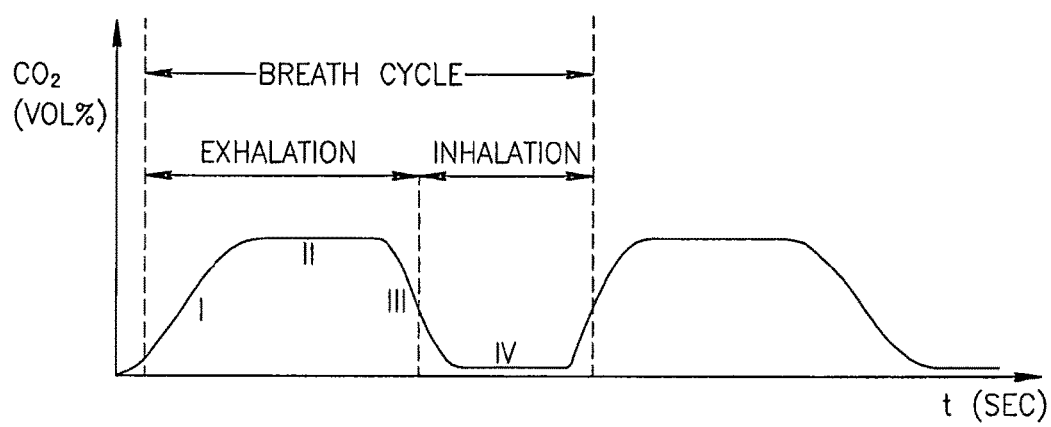
FIG. 1—a schematic exemplary graph of a series of consecutive breath cycles.

In the following description, various aspects of the disclosure will be described. For the purpose of explanation, specific configurations and details are set forth in order to provide a thorough understanding of the disclosure. However, it will also be apparent to one skilled in the art that the embodiments may be practiced without specific details being presented herein. Furthermore, well-known features may be omitted or simplified in order not to obscure the embodiments.

Measurements of rate parameters and the determination of the rate may not be straightforward, since there is no absolute rate, due to the fact that the measured rate may change as a function of the period used to calculate it. There is no standard defining a period over which the rate should be calculated. This becomes apparent for a parameter that may change over time, and especially for those that can change ad-hoc, fluctuate and trend at different rates such as, for example, the parameter of respiratory rate. In some cases, these types of parameters, such as respiratory rate, should be determined on-line, in real-time measurements. Furthermore, since there is no defined standard, when defining the period used for calculating a monitored rate, it should be take into consideration for whom, and for what reason the monitored parameter is defined. A period used for calculating a monitored rate may be a predetermined time period or a period defined by number of occurrences of events, wherein events may include any measurable health related parameter. For example, events may include breath cycle. If the information needed is for providing instantaneous on-line, real-time patient data to the health care providers and allowing them to react quickly to any dangerous new condition, then the said period should, on the one hand, be reasonably short, but on the other hand be long enough so as not to set off an alarm on every artifact, or short, insignificant event. This is also correct for parameters where a value is measured substantially instantaneously, such as for example the measurement of $EtCO_2$, the measurement of changes in $CO_2$ levels ($CO_2$ patterns), $CO_2$ waveform, and the like. If the parameter of interest is a measurement that can fluctuate because of different artifacts or medical reasons, the values may be best displayed as an average over a defined time period. The time period used may be calculated based on the minimal limit determined for this parameter and depending on the use that the data is being provided for. Consequently, the meaningfulness of any medical parameter is very much a function of the period the value was averaged over, or the rate from which it was calculated. Furthermore, for different medical environments and health care settings there may be several rationales that may often be conflicting for defining a period for measurements and hence for the rate or average calculations.

The requirement of reliably defining the time period for measurements and calculations becomes even more significant when defining alarm limits for a medical monitoring device. An alarm may be triggered when the measured parameter reading reaches a defined threshold. That threshold may be reached at different time intervals for different definitions of the said time period. However, the assessment of issuing an alarm should also take into consideration the need to minimize non-clinically significant alarms (those that result from artifacts and do not indicate an authentic significant clinical change) over genuine alarms (those that result from authentic/significant clinical change).

According to some embodiments, there are thus provided methods for measuring and averaging the respiratory rate while reducing the number of non-clinically significant alarms. This may be performed by using an adaptive averaging time that may change in accordance with the status of stability of the patient. For example, the averaging time may be longer or shorter during instability or stability periods, respectively.

As referred to herein, the terms "health care provider(s)" and "medical staff" may interchangeably be used. The terms may include any health care professional that may monitor, treat, check, examine, and the like, a patient. For example, a health care provider may include a physician, a nurse, and the like.

As referred to herein, the term "respiratory rate", "respiration rate" and "breath rate" may interchangeably be used and relate to the number of breaths/breath cycles a subject is taking in a minute and is expressed in units of breaths per minute (BPM).

As referred to herein, the terms, "alarm" and "alert" may interchangeably be used.

As referred to herein, the terms "dynamically" and "in real-time" may interchangeably be used.

A basic, minimal limit for measuring breath rate is the length of one breath cycle, which includes the stages of exhalation and inhalation. Reference is now made to FIG. 1, which depicts a schematic graph of a series of consecutive breath cycles. As shown in FIG. 1, the breath cycle depicts the change in expired $CO_2$ Vol (%, y-axis) over time (t, X-axis). Such a graph is also known as a $CO_2$ waveform. In general, the breath cycle may be divided into two main phases: the exhalation phase ("exhalation", FIG. 1), in which the $CO_2$ levels are highest, and the inhalation phase ("inhalation" FIG. 1), in which $CO_2$ levels are minute. The length of one breath cycle is defined by two consecutive exhalation phases ("breath cycle", FIG. 1). At first, the levels of $CO_2$ increase (stage I in the graph of FIG. 1) as a result of $CO_2$ release from the airways, from what is known as the "dead space", which is the space in which no gas exchange takes place. Then, the $CO_2$ reaches a plateau at high levels of $CO_2$, which corresponds to the release of $CO_2$ from the lungs, in the exhalation phase (step II in the graph of FIG. 1). The decline in $CO_2$ levels (stage III in the graph of FIG. 1) is followed by the inhalation phase (stage IV in the graph of FIG. 1), which is characterized by absence/minute levels of $CO_2$.

The normal respiratory rate may change with age and under various physiological conditions, such as exercise, excitement, pain, crying and other conditions. The rate may vary as much as from 5 BPM (in adults) to 150 BPM (in neonatal). For example: newborns may average about 44 BPM, infants may average about 20-40 BPM, preschool children may average about 23-30 BPM, children may average about 16-25 BPM and adults may average about 12-20 breaths per minute. The respiratory rate may be indicative of a number of medical conditions, such as, for example: fever, over-sedation and respiratory problems (such as a hypoventilation condition that may be by itself a predictor for central apnea). In addition, various medical conditions may cause changes between short and long breaths, and changes may occur over short periods of time. In this regard it is noted that erratic breathing patterns are synonymous with healthier patients, whereas highly organized waveforms are more synonymous with ill patients.

A need for evaluating the respiratory rate may arise with various medical conditions. For example, a significant need for evaluating the respiratory rate may arise in situations such as, for example, pain management or sedation. Pain management may include the management of patients that have undergone surgery and/or patients that undergo periodic, painful procedures (such as in the oncology department). In this environment, patients are titrated with high levels of pain relievers (such as opiates), sedatives and analgesic medications. Monitoring of such patients is of high importance, as the health care providers may not always be aware of how an individual patient may react to a level of any of the medications (some patients may be more susceptible than others). Furthermore, in pain management to date, there is a trend to allow a patient to titrate his own needs for the medications, since only the patient feels the level of pain he is in and his ability to withstand it. These factors strongly increase the need for patient monitoring so that any adverse affects may be detected at an early stage. Such an example is the need to detect hypoventilation, which is a medical condition wherein breath is too shallow or too slow and is not adequate to meet the needs of the body and is often the event preceding the more dangerous condition of central apnea. Hypoventilation may be diagnosed by detecting low respiratory rates that may occur, for example, by over-dosing by medication. Hypoventilation with sedated patients may be recognized by a falling respiratory rate (often together with increased $EtCO_2$ readings), in which case an alarm indicating such a condition is required. However, the question remains as to when the health care provider can reliably be warned that the patient has reached such a condition. The longer the respiratory rate measurement interval is, there is a higher degree of assurance that a reliable respiratory rate result was obtained, for example in detecting a low respiratory rate. On the other hand, the longer the respiratory rate measurement interval is, a condition that started minutes back may be neglected, and hence the patient may be placed in danger. Moreover, a lower respiratory rate may be defined to trigger an alarm, but again, an important indication may possibly be neglected, even though the patient has yet to reach the defined low threshold limit.

Measuring the respiratory rate in a short period of time or using a high threshold of respiratory rate to indicate a clinical situation may result in a large percent of non-clinically significant alarms, where there was no real need for any medical attention at all. Moreover, too many false (non-clinically significant) alarms promotes a "cry wolf" situation, where alarms are disregarded even when important. In addition, in pain management, the alarms tend to become an annoyance also to the patient and his family, even if perceived to be of no medical value.

According to some embodiments, measurements of health related parameters, such as, for example, respiratory rate, may be performed over any period of time, such as, for example, in the range of about 15 to 180 seconds. Measurement of health related parameters, such as breath rate, may also be performed over a period of time which may be determined according to the number of occurrences of events of the health related parameter. For example, regarding breath rate measurements, a period of time may be determined by the time period required for X number of breath cycles to occur, wherein X may be, for example, in the range of 2-15 breath cycles. Herein, embodiments referring to measurements over a predetermined period of time (such as, for example, number of seconds) and measurements over a period time, wherein the time period may be determined by the occurrence of predetermined number of events (such as for example number of breath cycles), may interchangeably be practiced.

There is thus provided, according to some embodiments, a method for real-time measuring of a breath related parameter, the method including measuring a breath related parameter, such as, for example, respiratory rate, over a predetermined period of time, wherein the results of the measurement are averaged over that period of time and may further be normalized to 1 minute so as to obtain the result in units of breaths per minute (BPM). The method may include measuring a breath related parameter, such as, for example, respiratory rate, over a period of time that is determined by number of occurrences of events of that parameter, wherein the results of the measurement are averaged over that period of time. For example, the time period for the calculation of the average respiratory rate may also be calculated by measuring the time period over which a predetermined number of breath cycles have occurred. The method may include the use of various algorithms for calculating the breath related parameter (for example, respiratory rate) and the average breath related parameter (for example, the respiratory rate).

According to some exemplary embodiments, the breath related parameter measurements may be performed over any time period length of between 15 seconds to 3 minutes, and the average measurement may then be calculated. For example, respiratory rate measurements may be performed over any time period in the length of between 30 seconds up to 2 minutes and the respiratory rate, expressed in units of breaths per minute (BPM), may then be averaged accordingly. The average BPM may be calculated by multiplying or dividing the measurements by the measured time period, so that rate would display breaths number per minute. For example, the number of breaths (breath cycles) may be measured over 30 seconds, and the average BPM would then be calculated by multiplying the number of measured breaths by 2, so that the number of breaths per minute is obtained. For example, the number of breaths (breath cycles) may be measured over 2 minutes, and the average BPM would then be calculated by dividing the number of measured breaths by 2, so that the number of breaths per minute is obtained.

According to some embodiments, the breath related parameter (such as respiratory rate) measurement may be performed over any time period that may be determined by number of occurrences 2-20 breath cycles and the average measurement may then be calculated accordingly.

According to some embodiments, the method for real-time measuring of a breath related parameter may further include setting off an alarm if a threshold limit of the measured parameter is reached. For example, regarding respiratory rate, a lower threshold limit may be set to any number of BPM, under which an alarm is set off. For example, an upper threshold limit may be set to any number of BPM, over which an alarm is set off. For example, an alarm may be set off if the respiratory rate reaches a lower threshold limit that may be any number of BPM in the range of 4 to 16.

Several clinical trials have shown that increasing the time period of the measurements based on which the average BPM is calculated may result in lowering the number of non-clinically significant alarms. For example, clinical trials performed on several hundreds of patients in a pain management environment have demonstrated that setting a lower threshold limit of 6 BPM and increasing the time period of the measurement based on which the average BPM is calculated from 30 seconds to 60 seconds, results in approximately a 68% decrease in the number of non-clinically significant alarms (that is, only 32% of non-clinically-significant alarms were set off), compared to the number of non-clinically significant alarms when the average BPM was calculated over a 30 second time period. Increasing the time period of the measurement based on which the average BPM is calculated from 30 seconds to 90 seconds, results in approximately an 85% decrease in the number of non-clinically significant alarms (that is, only 15% of non-clinically-significant alarms were set off), compared to the number of non-clinically significant alarms when the average BPM was calculated over a 30 second time period. Increasing the time period of the measurement based on which the average BPM is calculated from 30 seconds to 120 seconds, results in approximately a 93% decrease in the number of non-clinically significant alarms (that is, only 7% of non-clinically-significant alarms were set off), compared to the number of non-clinically significant alarms when the average BPM was calculated over a 30 second time period.

Clinical trials performed on several hundreds of patients in a pain management environment have shown that setting a lower threshold limit of 8 BPM and increasing the time period of the measurement based on which the average BPM is calculated from 30 seconds to 60 seconds, results in approximately a 52% decrease in the number of non-clinically significant alarms (that is, only 48% of non-clinically-significant alarms were set off), compared to the number of non-clinically significant alarms when the average BPM was calculated over a 30 second time period. Increasing the time period of the measurement based on which the average BPM is calculated from 30 seconds to 90 seconds, results in approximately a 78% decrease in the number of non-clinically significant alarms set off (that is, only 22% of non-clinically-significant alarms were set off), compared to the number of non-clinically significant alarms when the average BPM was calculated over a 30 second time period. Increasing the time period of the measurement based on which the average BPM is calculated from 30 seconds to 120 seconds, result in approximately an 88% decrease in the number of non-clinically significant alarms (that is, only 12% of non-clinically-significant alarms were set off), compared to the number of non-clinically significant alarms when the average BPM was calculated over a 30 second time period.

Clinical trials performed on several hundreds of patients in a pain management environment have shown that setting a lower threshold limit of 10 BPM and increasing the time period of the measurement based on which the average BPM is calculated from 30 seconds to 60 seconds, results in approximately a 56% decrease in the number of non-clinically significant alarms (that is, only 44% of non-clinically-significant alarms were set off), compared to the number of non-clinically significant alarms when the average BPM was calculated over a 30 second time period. Increasing the time period of the measurement based on which the average BPM is calculated from 30 seconds to 90 seconds, results in approximately a 68% decrease in the number of non-clinically significant alarms (that is, only 32% of non-clinically-significant alarms were set off), compared to the number of non-clinically significant alarms when the average BPM was calculated over a 30 second time period. Increasing the time period of the measurement based on which the average BPM is calculated from 30 seconds to 120 seconds, results in approximately a 77% decrease in the number of non-clinically significant alarms (that is, only 23% of non-clinically-significant alarms were set off), compared to the number of non-clinically significant alarms when the average BPM was calculated over a 30 second time period.

Clinical trials performed on several hundreds of patients in a pain management environment have shown that, setting a lower threshold limit of 12 BPM and increasing the time period of the measurement based on which the average BPM is calculated from 30 seconds to 60 seconds, results in approximately a 55% decrease in the number of non-clinically significant alarms (that is, only 45% of non-clinically-significant alarms were set off), compared to the number of non-clinically significant alarms when the average BPM was calculated over a 30 second time period. Increasing the time period of the measurement based on which the average BPM is calculated from 30 seconds to 90 seconds, results in approximately a 70% decrease in the number of non-clinically significant alarms (that is, only 30% of non-clinically-significant alarms were set off), compared to the number of non-clinically significant alarms when the average BPM was calculated over a 30 second time period. Increasing the time period of the measurement based on which the average BPM is calculated from 30 seconds to 90 seconds, results in approximately a 78% decrease in the number of non-clinically significant alarms (that is, only 22% of non-clinically-significant alarms were set off), compared to the number of non-clinically significant alarms when the average BPM was calculated over a 30 second time period.

However, merely increasing the averaging time and changing the threshold level of setting an alarm, although it may yield a lower number of non-clinically significant alarms, may, in some cases miss out on clinically significant events that may be unattended to in a timely manner because of the longer averaging time. There may be many instances where, for short periods of time, a patient may stop breathing, for example, when holding his breath in deep pain, or because of airway obstruction. During such instances, the respiratory rate may drop drastically, even if the breath paused for a short period of time (such as, for example, 15 seconds), triggers an alarm. Hence, there is a need to define a method, such as an algorithm, for creating a respiratory rate value that depicts more rhythms or rates, and not short-lived events.

According to some embodiments, there is thus further provided a method for measuring a breath related parameter, such as, but not limited to, respiratory rate, $CO_2$ waveform (see FIG. 1), $EtCO_2$, Pulmonary index (such as an index described below), and the like. The method includes measuring a breath related parameter over a period of time wherein the result of the measurement is averaged over the period of time and wherein the period of time is adapted to change according to the results of the measurement of the breath related parameter.

According to some embodiments, there is further provided a method for measuring a breath related parameter, such as but not limited to, respiratory rate, $CO_2$ waveform, $EtCO_2$, Pulmonary index, and the like, or any combination thereof. The method includes measuring a breath related parameter during a period of time that is determined by a number of occurrences of events, such as the number of breath cycles, wherein the result of the measurement is averaged by averaging calculation over the period of time that is determined by the number of occurrences of events and wherein the number of occurrences of events are adapted to change according to the result of the measurement of the breath related parameter. For example, instead of measuring over a predetermined period of time, such as, for example, 60 seconds, the measurement may be performed upon whatever period of time required for breathing a predetermined number of breath cycles, such as, for example 8 (or any other number, such as a number in the range of 2-20) breath cycles. The result may then be averaged accordingly.

According to some exemplary embodiments, regarding the respiratory rate as a breath related parameter, one method of calculating the average respiratory rate may include measuring the number of breath cycles (breaths) that occurred over a time period, and then normalizing the results to how many breaths occur in one minute (expressed in units of breaths per minute (BPM). Another method of calculating the average respiratory rate may include measuring the number of breath cycles that occurred over a time period, calculating the average time of a breath cycle and accordingly calculating the average BPM.

For example, the time period for measuring and averaging BPM may be changed according to the calculated average of BPM. For example, the averaging time may be shortened if the average BPM is higher than a predetermined threshold.

For example, the averaging time may be a time period of 30 seconds, if the respiratory rate is 15 BPM (a respiratory rate that is synonymous with a healthy patient). The averaging time may be longer if the average BPM is lower than a predetermined threshold. For example, averaging time may be a time period of 120 seconds if the respiratory rate is 6 BPM (a respiratory rate that is synonymous with a patient entering hypoventilation).

According to some embodiments, there is further provided a method for measuring a breath related parameter, such as but not limited to, respiratory rate, $CO_2$ waveform, Pulmonary index, and the like, or any combination thereof. The method includes measuring a breath related parameter over a period of time wherein the result of the measurement is averaged by a weighted averaging calculation. The weighted averaging calculation may be performed over that period of time, which is further adapted to change according to the results of the measurement of the breath related parameter.

According to some embodiments, there is further provided a method for measuring a breath related parameter, such as but not limited to, respiratory rate, $CO_2$ waveform, Pulmonary index, and the like, or any combination thereof. The method includes measuring a breath related parameter during a period of time that may be determined by the number of occurrences of events, (such as for example the time period required for an X number of breath cycles to occur). The result of the measurement may then be averaged by a weighted averaging calculation over that time period and wherein the number of occurrences of events is adapted to change according to the result of the measurement of the breath related parameter.

For example, a more sophisticated and complex algorithm may be used in real-time, wherein the averaged breath related parameter is not calculated merely as a simple average, but rather different levels of weighting may be given to various parameter characteristics (such as temporal characteristics) during the measurements. For example, the averaged BPM is not calculated as a simple average but rather different levels of weighting are given to different breaths during the measurements, such as for example, the last N number of breaths are given a different level of weighting when average is calculated. N may be any number of between 2 to 18.

According to some embodiments, an algorithm may be used to calculate the average BPM by measuring number of breaths over a time period in the range of from about 15 seconds to 2 minutes, wherein the last N number of breaths is given a higher level of weighting when the average is calculated. N may be any number of breaths in the range of from 2 to 18. For example, an algorithm may be used to calculate the average BPM by measuring number of breaths over a time period of 120 seconds, wherein the last 3 breaths are given a higher level of weighting when the average is calculated.

According to some embodiments, an algorithm may be used to calculate the average BPM by measuring number of breaths over a time period in the range of from about 15 seconds to 2 minutes, wherein the first N number of breaths is given a higher level of weighting when the average is calculated. N may be any number of breaths in the range of from 2 to 18. For example, an algorithm may be used to calculate the average BPM by measuring breath number over a time period of 120 seconds, wherein the first 3 breaths are given a higher level of weighting when the average is calculated.

According to some embodiments, an algorithm may be used to calculate the average BPM by measuring number of breaths over a time period in the range of from about 15 seconds to 2 minutes, wherein the first N number of breaths and the last N number of breaths are given a higher level of weighting when the average is calculated. N may be any number of breaths in the range of from 2 to 18. For example, an algorithm may be used to calculate the average BPM by measuring number of breaths over a time period of 120 seconds, wherein the first 3 breaths and the last 3 breaths are given a higher level of weighting when the average is calculated.

According to some embodiments, an algorithm may be used to calculate the average BPM by measuring number of breaths over a time period in the range of from about 15 seconds to 2 minutes, wherein the N number of breaths that are between the first N1 breaths and the last N2 breaths are given a higher level of weighting when the average is calculated. N may be any number of breaths in the range of from 2 to 17. N1 and N2 may be any number of breaths in the range of from 1 to 18. For example, an algorithm may be used to calculate the average BPM by measuring number of breaths over a time period of 120 seconds, wherein the breaths that are between the first 2 breaths and the last 2 breaths are given a higher level of weighting when the average is calculated.

According to some embodiments, the averaged BPM may be calculated as a weighted average wherein different levels of weighting are given to different breaths during the measurements, based on the measured breath rate. Meaning that the weighting may be determined as a function of the measured breath rate. For example, if the measured breath rate is higher than a predetermined value, the last N numbers of breaths are given a higher level of weighting when average is calculated. If the measured breath rate is lower than a predetermined value, the first N numbers of breaths are given a higher level of weighting when average is calculated. N may be any number of between 2 to 18.

According to some embodiments, an algorithm may be used to calculate the average BPM by measuring number of breaths over a time period in the range of from about 15 seconds to 2 minutes. If the measured breath rate is higher than Y1, the last N numbers of breaths are given a higher level of weighting. If the measured breath rate is lower than Y2, the first N numbers of breaths are given a higher level of weighting when the average is calculated. N may be any number of breaths in the range of from 2 to 18. Y1 may be any number higher than 10. Y2 may be any number lower than 10. For example, an algorithm may be used to calculate the average BPM by measuring number of breaths over a time period of 120 seconds. If the measured respiratory rate is higher than 12, the last 3 breaths are given a higher level of weighting when the average is calculated. If the measured respiratory rate is lower than 8, the first 3 breaths are given a higher level of weighting when the average is calculated.

According to some embodiments, there is provided a method for measuring a breath related parameter, the method including: measuring a breath related parameter (such as, for example, but not limited to, respiratory rate, $CO_2$ waveform, Pulmonary index, and the like, or any combination thereof) over a first period of time, wherein the result of the measurement is averaged (optionally by weighted averaging) over the first period of time; obtaining a breath related value(s) over a second period of time, wherein the result is averaged (optionally by weighted averaging) over the second period of time; and wherein the first and optionally the second period(s) of time is (are) adapted to change according to the result of the measurement of the breath related parameter and/or the breath related value(s). The periods of time may be a predetermined period of time, (such as for example number of seconds) or a period of time determined by number of occurrences of events, (such as for example, number of breath cycles). In addition, various algorithms and/or additional mathematical filters, either known today or to be developed in the future may also be implemented in the method.

According to some embodiments, the breath related parameter may include for example, such parameters as, but not limited to: respiratory rate, $CO_2$ waveform patterns, Pulmonary index, $CO_2$ concentration in the ventilated breath, $EtCO_2$, and the like, or any combination thereof. The breath related value may be obtained from a direct measurement of various breath related parameters or may be obtained indirectly (for example, by computation) from measurements of various breath related parameters. The breath related value, received in real-time, may be indicative of the reliability, trustworthiness and consistency of the breath related parameter being measured. The breath related value may then be used to dictate in real-time the level of averaging and/or the time period used for calculating the average of the breath related parameter that is being measured and monitored. For example, regarding breath rate measurements, if the breath related value indicates inconsistency, then the averaging time, or time period used for calculating the breath rate may be increased, since generally, more erratic breathing patterns are synonymous with healthier patients. On the other hand if there is strong consistency, the averaging time, or time period used for calculating the breath rate may be reduced, since generally, highly organized breathing patterns (such as demonstrated by the breath cycles waveforms) are more synonymous with ill patients.

According to some embodiments, the breath related value may be one or more measured or calculated breath related values. For example, the second breath related value may be, for example one or more values of a breath cycle (such as shown in FIG. 1), such as, for example, breath cycle waveform shape, slopes of the various stages of the waveform, area of the various stages of the waveform, integral ratio between inhalation and exhalation stages of the breath cycle, ratio between time of the inhalation and exhalation stages, amplitude (intensity) of the breath cycle, standard deviations of the breath cycle(s), variance of the breath cycle(s), dispersion of the breath cycle(s), and the like, or any combination thereof may be used as a breath related value. The breath related value may further include the respiratory rate; $CO_2$ waveform patterns; EtCO2; and the like, or any combination thereof.

According to some embodiments, adding the breath related value may indicate consistency and stable trends, or oppositely, indicate inconsistency and thus may enable dangerous conditions to be detected early, while non-clinical artifacts (non-clinically significant events) may be lost within the long averaging periods.

According to some embodiments, the breath related parameter may be the main parameter being measured and monitored. The breath related value may be a secondary value being obtained, according to which the real-time level of averaging and/or the time period used for calculating the average of the breath related parameter may be determined.

According to some embodiments, the results may stem in an adaptive window, where the breath related value may be used to control, in real-time, the extent of averaging, and/or the time period for calculation of the breath related parameter being monitored. This way, the number of false, non-clinically significant alarms may be considerably reduced without any need to increase averaging periods or providing more extreme alarm limits, which may waste valuable time before a health care provider will react to the event. In addition, this adaptive window can also be associated with how close the breath related parameter is from the defined alarm limits, hence, when reaching close to the limits, averaging time and/or extent of averaging may be changed accordingly.

According to some embodiments, the breath related values may be obtained based on measurements from time periods in the range of from 5 seconds to 3 minutes that may be taken in parallel with the breath related parameter. The breath related values may also be based on measurements taken over a time period in the range of from 5 seconds to 3 minutes beforehand, or in addition, when the breath related parameter measurements were taken. The breath related values may be obtained based on measurements from time periods that are determined according to number of occurrences of events, such as, for example, the time period needed for a given number of breath cycles (for example, in the range of 2 to 20), to occur.

According to some exemplary embodiments, if the respiratory rate is the breath related parameter being monitored, any number of seconds in the range of 15-120 seconds may be used for calculating the average respiratory rate. The breath related value may be measured/calculated in parallel with the respiratory rate in a time period in the range of 15-120 seconds. Alternatively, the breath related value may be measured over any number of seconds in the range of 5-360 seconds, prior to the measurements of the breath related parameter, that is, the respiratory rate. If the breath related value deviates from predetermined limits, the period for calculating the breath related parameter (that is breath rate) is changed accordingly to accommodate the new condition. The predetermined limits and ranges may be chosen by the user, or may be set as a function of other breath related parameters and/or values.

According to some embodiments, if the respiratory rate is the breath related parameter being monitored, any number of seconds in the range of 15-120 seconds may be used for calculating the average respiratory rate. The breath related value may be measured/calculated in parallel with the respiratory rate in a time period in the range of 15-120 seconds or over any time period prior to measurements of the respiratory rate. If the breath related value deviates from predetermined limits, the average value of the breath related parameter is not displayed (released) and data continues to be collected from the next breath cycles. The new data collected may now be part of the new measurements/calculations of the breath related value. If, after the new measurements/calculations, the breath related value still deviates from predetermined limits, the new average of the breath related parameter is not displayed (released) and the data continues to be collected and be part of the new measurements/calculations of the breath related value. If, within a predetermined time period of X, the breath related value still deviates from predetermined limits, the average value of the breath related parameter is displayed (released), and a new set of measurements/calculations may commence. The predetermined limits and ranges may be chosen by the user, or may be set as a function of other breath related parameters, (such as, for example, the breath rate itself, $CO_2$ waveform patterns, pulmonary index, and the like, or any combination thereof), and/or other breath related values. X may be any time range of 15-120 seconds.

According to some embodiments, the breath related value may be the breath cycle variance. The variance of the breath cycle may be the variance of any of the breath cycle related parameters, such as for example, breath cycle time, breath cycle rate, the ratio between the durations of the inhalation and the exhalation stages, slopes of the various breath cycle stages, or any other breath cycle related parameter or a combination of breath related parameters. The variance may be calculated as the average squared deviation of each breath cycle parameter from its mean. For example, the variance may be calculated as the average squared deviation of each breath cycle time from its mean within the measurement time period. For example, the variance may be calculated as the average squared deviation of each breath cycle rate from its mean within a predetermined number of breaths. For example, regarding $EtCO_2$ measurements, the variance may be calculated as the average squared deviation of each breath cycle integral ratio (and/or duration) between inhalation and exhalation stages from its mean within a predetermined number of breaths and/or predetermined time. The variance may also be related to the slopes, area and/or height of the breath cycle peaks and or the $CO_2$ waveform pattern. The variance may be represented by the formula $\sigma^2 = (\Sigma(x-\mu)^2)/$ N, wherein σ2 represents the variance, x represents breath cycle parameter (such as for example, time) and μ represent breath cycle parameter mean (such as for example, time). N represents number of breath cycles within the measurement time period or within the predetermined number of breaths.

According to some embodiments, the time period or the number of occurrences of events used for calculating the breath related value may remain fixed, independently of the calculated breath related value. However, according to additional embodiments, the time period or the number of occurrences of events used for the calculation of the breath related value may be changed as a function of the averaged breath related parameter. For example, if the breath related parameter is the breath rate, and the breath related value is the breath cycle variance, the time period or the number of occurrences of events over which the variance is calculated may change according to the final calculated average respiratory rate. For example, if the calculated respiratory rate is high (such as, for example, 10), then longer time period or higher number of occurrences of events (such as, for example, breath cycle) may be used for variance calculation and averaging calculation. For example, if the calculated respiratory rate is low (such as, for example, 5), then shorter time period or lower number of occurrences of events (such as, for example, breath cycle) may be used for variance calculation and averaging calculation.

According to some exemplary embodiments, the respiratory rate may be measured over time period in the range of 15-120 seconds. The breath related value may be obtained from measurements taken in parallel with the respiratory rate, over a fixed, predetermined time period, in the range of about 15-120 seconds. For example, the breath related value may be the breath cycle variance. If the breath cycle variance is below a given value, then the new respiratory rate is provided as the average over the predetermined time period. If the breath cycle variance (obtained from measurements taken in parallel with the breath rate) starts to increase, then the period for calculating the breath rate is increased accordingly. The time period/number of occurrences of events for calculating the breath related value, such as the breath cycle variance, may be fixed and does not change. The time period/number of occurrences of events according which the breath related parameter is averaged, may be changed according to the calculated variance. For example, the respiratory rate may be measured over a time period of 30 seconds. The breath related value may be the breath cycle variance and it may be obtained from measurements taken over a time period of 30 seconds, in parallel with the respiratory rate. If the breath cycle variance is below a given value of for example 2.7, then the new respiratory rate is provided as the average over the 30 second time period. If the breath cycle variance, obtained from measurements taken in parallel with the respiratory rate, starts to increase, then the period for calculating the breath rate is increased accordingly, for example to a time period of 60 seconds. The time period for obtaining the breath related value remains fixed at 30 seconds, regardless of changes in the breath related value.

According to some exemplary embodiments, if the respiratory rate is the breath related parameter being monitored, any number of seconds in the range of 15-120 seconds may be used for calculating the average respiratory rate. The breath related value may be obtained from measurements taken over a time period of 5 to 120 seconds before the respiratory rate is being measured. For example, the breath related value may be the breath cycle variance. If the breath cycle variance is below a given value, then the new respiratory rate is provided as the average over the predetermined time period. If the breath cycle variance (that is obtained from measurements taken over a time period preceding the measurement of the respiratory rate) starts to increase, then the time period for calculating the respiratory rate is increased accordingly. For example, the respiratory rate is measured over a time period of 30 seconds. The breath related value may be the breath cycle variance, and it may be obtained from measurements taken over a time period of 30 seconds, prior to measurements of the respiratory rate. If the breath cycle variance is below a given value, for example 2.7, then the new respiratory rate is provided as the average over the 30 second time period. If the breath cycle variance (that is obtained from measurements taken over a time period preceding the measurement of the respiratory rate) increases, then the period for calculating the breath rate is increased accordingly, for example to a time period of 60 seconds.

According to some embodiments, if the respiratory rate is the breath related parameter being monitored, any number of seconds in the range of 15-120 seconds may be used for calculating the average respiratory rate. The breath related value may be measured/calculated in parallel with the respiratory rate in a time period in the range of 15-120 seconds or over any time period prior to measurement of the respiratory rate. For example, the breath related value may be the breath cycle variance. If the breath cycle variance deviates from predetermined limits, the average value of the respiratory rate is not displayed (released) and data continues to be collected from the next breath cycles. The new data collected may now be part of the new measurements/calculations of the breath cycle variance. If the new breath cycle variance value still deviates from predetermined limits, the new average of the respiratory rate is not displayed (released) and the data continues to be collected and be part of the new measurements/calculations of the breath cycle variance. If within a predetermined time period of X, the breath cycle variance still deviates from predetermined limits, the average value of the respiratory rate is displayed (released), and the measurements may continue according to the last settings, or a new set of measurements/calculations may start. The predetermined limits and ranges may be chosen by the user, or may be set as a function of other breath related parameters and/or values. X may be any time period of between 15-120 seconds. For example, the respiratory rate may be measured over time a period in the range of 30 seconds. The breath cycle variance may be obtained from measurements taken in parallel with the respiratory rate. If the breath cycle variance is below a given value of for example, 2.7, then the new respiratory rate is provided as the average over the 30 second time period. If the breath cycle variance starts to increase, then the respiratory rate average and the breath cycle variance are recalculated by adding the measurements/calculations of the breath cycle variance of the next breath cycle to the calculations. If the new breath cycle variance thus obtained is within the predetermined limits of below 2.7, the new respiratory rate average is displayed (released). If the new breath cycle variance still deviates from the predetermined limits, then the respiratory rate average and the breath cycle variance are recalculated by adding the next measurement of the breath cycle variance to the calculations. If after a time period of 120 seconds, the breath cycle variance still deviates from predetermined limits, the respiratory rate average is displayed (released) and a new set of measurements/calculations commences.

According to other embodiments, if the respiratory rate is the breath related parameter being monitored, any number of seconds in the range of 15-120 seconds may be used for calculating the average respiratory rate. The breath related value may be measured/calculated in parallel with the respiratory rate in a time period in the range of 15-120 seconds or over any time period prior to measurement of the respiratory rate. For example, the breath related value may be the breath cycle variance. If the breath cycle variance deviates from predetermined limits, the average value of the respiratory rate is not displayed (released) and data continues to be collected from the next breath cycles. The new data collected may now be part of the new measurements/calculations of the breath cycle variance, however, the time period over which the variance is calculated remains fixed. If the new the breath cycle variance value still deviates from predetermined limits, the new average of the respiratory rate is not displayed (released) and the data continues to be collected and be to part of the new measurements/calculations of the breath cycle variance, the time period over which the variance is calculated remains fixed. If within a predetermined time period of X, the breath cycle variance still deviates from predetermined limits, the average value of the respiratory rate is displayed (released) and the measurements may continue according to the last settings, or a new set of measurements/calculations may start. The predetermined limits and ranges may be chosen by the user, or may be set as a function of other breath related parameters and/or values. X may be any time period of between 15-120 seconds. For example, the respiratory rate may be measured over a time period in the range of 30 seconds. The breath cycle variance may be obtained from measurements taken in parallel with the respiratory rate. If the breath cycle variance is below a given value of for example, 2.7, then the new respiratory rate is provided as the average over the 30 second time period. If the breath cycle variance starts to increase, then the respiratory rate average and the breath cycle variance are recalculated by adding the measurements/calculations of the breath cycle variance of the next breath cycle to the calculations. The variance is calculated according to the time period of the last 30 seconds. If the new breath cycle variance thus obtained is within the predetermined limits of below 2.7, the new respiratory rate average is displayed (released). If the new breath cycle variance still deviates from the predetermined limits, then the respiratory rate average and the breath cycle variance are recalculated by adding the next measurement of the breath cycle variance to the calculations. The variance is calculated according to the time period of the last 30 seconds. If after a time period of 120 seconds, the breath cycle variance still deviates from predetermined limits, the respiratory rate average is displayed (released) and the measurements may continue according to the last settings, or a new set of measurements/calculations may start.

According to some embodiments, the breath related value may be the breath cycle period standard deviation. The standard deviation may be calculated as the square root of the breath cycle variance.

According to some exemplary embodiments, the respiratory rate may be measured over a time period in the range of 15-120 seconds. The breath related value may be obtained from measurements taken in parallel with the respiratory rate. For example, the breath related value may be the breath cycle period standard deviation.

If the breath cycle standard deviation is below a given value, the new respiratory rate is provided as the average over the predetermined time period. If the breath cycle standard deviation (obtained from measurements taken in parallel with the breath rate measurements) starts to increase, the time period for calculating the breath rate is increased accordingly.

According to some preferred embodiments, the respiratory rate may be measured over a time period of 30 seconds. The breath related value may be the breath cycle standard deviation, and it may be measured over a time period of 30 seconds, in parallel with the respiratory rate. If the breath cycle standard deviation is below a given value of 1.5, then the new respiratory rate is provided as the average over the 30 second time period. If the breath cycle standard deviation, obtained in parallel with the breath rate, starts to increase, then the period for calculating the breath rate is increased accordingly, for example to a time period of 60 seconds.

According to some exemplary embodiments, if the respiratory rate is the breath related parameter being monitored, any number of seconds in the range of 15-120 may be defined for calculating the respiratory rate. The breath related value may be obtained from measurements taken over a time period of 5 to 120 seconds before the respiratory rate is being measured. For example, the breath related value may be the breath cycle standard deviation. If the breath cycle standard deviation is below a given value, then the new respiratory rate is provided as the average over the predetermined time period. If the breath cycle standard deviation (that is obtained from measurements taken over a time period preceding the measurement of the respiratory rate) starts to increase, then the period for calculating the respiratory rate is increased accordingly.

According to some preferred embodiments, the respiratory rate may be measured over a time period of 30 seconds. The breath related value may be the breath cycle standard deviation and it may be obtained from measurements taken over a time period of 30 seconds, prior to the measurements of the respiratory rate. If the breath cycle standard deviation is below a given value of 1.5, then the new respiratory rate is provided as the average over the 30 second time period. If the breath cycle standard deviation, (obtained from measurements taken over a time period preceding the measurement of the respiratory rate) increases, then the period for calculating the breath rate is increased accordingly, for example to a time period of 60 seconds.

According to some embodiments, if the respiratory rate is the breath related parameter being monitored, any number of seconds in the range of 15-120 seconds may be used for calculating the average respiratory rate. The breath related value may be measured/calculated in parallel with the respiratory rate in a time period in the range of 15-120 seconds, or over any time period prior to measurement of the respiratory rate. For example, the breath related value may be the breath cycle standard deviation. If the breath cycle standard deviation deviates from predetermined limits, the average value of the respiratory rate is not displayed (released) and data continues to be collected from the next breath cycles. The new data collected may now be part of the new measurements/calculations of the breath cycle standard deviation. If the new breath cycle standard deviation value still deviates from predetermined limits, the new average of the respiratory rate is not displayed (released) and the data continues to be collected and be part of new measurements/calculations of the breath cycle standard deviation. If within a predetermined time period of X, the breath cycle standard deviation still deviates from predetermined limits, the average value of the respiratory rate is displayed (released) and the measurements may continue according to the last settings, or a new set of measurements/calculations may start. The predetermined limits and ranges may be chosen by the user, or may be set as a function of other breath related parameters and/or values. X may be any time period of between 15-120 seconds.

According to some exemplary embodiments, the respiratory rate may be measured over a time period in the range of 30 seconds. The breath cycle standard deviation may be obtained from measurements taken in parallel with the respiratory rate. If the breath cycle standard deviation is below a given value of, for example, 1.5, then the new respiratory rate is provided as the average over the 30 second time period. If the breath cycle standard deviation starts to increase, then the respiratory rate average and the breath cycle standard deviation are recalculated by adding the measurements/calculations of the breath cycle standard deviation of the next breath cycle to the calculations. If the new breath cycle standard deviation thus obtained is within the predetermined limits of below 1.5, the new respiratory rate average is displayed (released). If the new breath cycle standard deviation still deviates from the predetermined limits, then the respiratory rate average and the breath cycle standard deviation are recalculated by adding the next measurement of the breath cycle standard deviation to the calculations. If, after a time period of 120 seconds, the breath cycle standard deviation still deviates from predetermined limits, the respiratory rate average is displayed (released) and the measurements may continue according to the last settings, or a new set of measurements/calculations may start.

According to some embodiments, the breath related value may be the breath cycle dispersion, also referred to herein as the variability index. The breath cycle dispersion may be calculated by dividing the breath cycle variance by the breath cycles mean, as measured over the predetermined period of time or predetermined number of breaths. Alternately, the breath cycle dispersion may be calculated by dividing the breath cycle standard deviation by the breath cycles mean, as measured over the predetermined period of time or predetermined number of breaths.

According to some exemplary embodiments, the respiratory rate may be measured over a time period in the range of 15-120 seconds. The breath related value may be obtained from measurements taken in parallel with the respiratory rate. For example, the breath related value may be the breath cycle dispersion. If the breath cycle dispersion is below a given value, then the new respiratory rate is provided as the average over the predetermined time period. If the breath cycle dispersion, (obtained from measurements taken in parallel with respiratory rate) starts to increase, then the period for calculating the breath rate is increased accordingly. For example, the respiratory rate may be measured over a time period of 30 seconds. The breath related value may be the breath cycle dispersion, and it may be obtained from measurements taken over a time period of 30 seconds, in parallel with the respiratory rate. If the breath cycle dispersion, calculated by using the breath cycle variance, is below a given value of 25%, then the new respiratory rate is provided as the average over the 30 second time period. If the breath cycle dispersion, calculated by using the breath cycle standard deviation is below a given value of 15%, then the new respiratory rate is provided as the average over the 30 second time period. If the breath cycle dispersion, (obtained from measurements taken in parallel with the respiratory rate), starts to increase, then the period for calculating the breath rate is increased accordingly, for example to a time period of 60 seconds.

According to some exemplary embodiments, if the respiratory rate is the breath related parameter being monitored, any number of seconds in the range of 15-120 seconds may be used for calculating the average respiratory rate. The breath related value may be obtained from measurements taken over a time period of 5 to 120 seconds before the respiratory rate is being measured. For example, the breath related value may be the breath cycle dispersion. If the breath cycle dispersion, calculated by using the breath cycle variance, is below a given value of 25%, then the new respiratory rate is provided as the average over the 30 second time period. If the breath cycle dispersion, calculated by using the breath cycle standard deviation, is below a given value of 15%, then the new respiratory rate is provided as the average over the 30 second time period. If the breath cycle dispersion (that is obtained from measurements taken over a time period preceding the measurement of the respiratory rate) starts to increase, then the period for calculating the respiratory rate is increased accordingly. For example, the respiratory rate may be measured over a time period of 30 seconds. The breath related value may be the breath cycle dispersion, and it may be obtained from measurements taken over a time period of 30 seconds, prior to measurements of the respiratory rate. If the breath cycle dispersion, calculated by using the breath cycle variance is below a given value of 25%, then the new respiratory rate is provided as the average over the 30 second time period. If the breath cycle dispersion, calculated by using the breath cycle standard deviation is below a given value of 15%, then the new respiratory rate is provided as the average over the 30 second time period. If the breath cycle dispersion (that is obtained from measurements taken over a time period preceding the measurement of the respiratory rate) increases, then the period for calculating the breath rate is increased accordingly, for example to a time period of 60 seconds.

According to some embodiments, if the respiratory rate is the breath related parameter being monitored, any number of seconds in the range of 15-120 seconds may be used for calculating the average respiratory rate. The breath related value may be measured/calculated in parallel with the respiratory rate in a time period in the range of 15-120 seconds or over any time period prior to measurement of the respiratory rate. For example, the breath related value may be the breath cycle dispersion. If the breath cycle dispersion deviates from predetermined limits, the average value of the respiratory rate is not displayed, and data continues to be collected from the next breath cycles. The new data collected may now be part of the new measurements/calculations of the breath cycle dispersion. If the new breath cycle dispersion value still deviates from predetermined limits, the new average of the respiratory rate is not displayed (released) and the data continues to be collected and to be part of new measurements/calculations of the breath cycle dispersion. If within a predetermined time period of X, the breath cycle dispersion still deviates from predetermined limits, the average value of the respiratory rate is displayed (released) and a new set of measurements/calculations may commence. The predetermined limits and ranges may be chosen by the user, or may be set as a function of other breath related parameters and/or values. X may be any time period of between 15-120 seconds.

According to some exemplary embodiments, the respiratory rate may be measured over a time period in the range of 30 seconds. The breath cycle dispersion may be obtained from measurements taken in parallel with the respiratory rate. If the breath cycle dispersion is below a given value of, for example, 25% (if calculated by using the breath cycle variance) or 15% (if calculated by using the breath cycle standard deviation), then the new respiratory rate is provided as the average over the 30 second time period. If the breath cycle dispersion starts to increase, then the respiratory rate average and the breath dispersion are recalculated by adding the measurements/calculations of the breath cycle dispersion of the next breath cycle to the calculations. If the new breath cycle dispersion thus obtained is within the predetermined limits of below 25% (if calculated by using the breath cycle variance) or 15% (if calculated by using the breath cycle standard deviation), the new respiratory rate average is displayed (released). If the new breath cycle dispersion still deviates from the predetermined limits, then the respiratory rate average and the breath cycle dispersion are recalculated by adding the next measurement of the breath cycle dispersion to the calculations. If, after a time period of 120 seconds, the breath cycle dispersion still deviates from predetermined limits, the respiratory rate average is displayed (released) and a new set of measurements/calculations commences.

Figure 2:
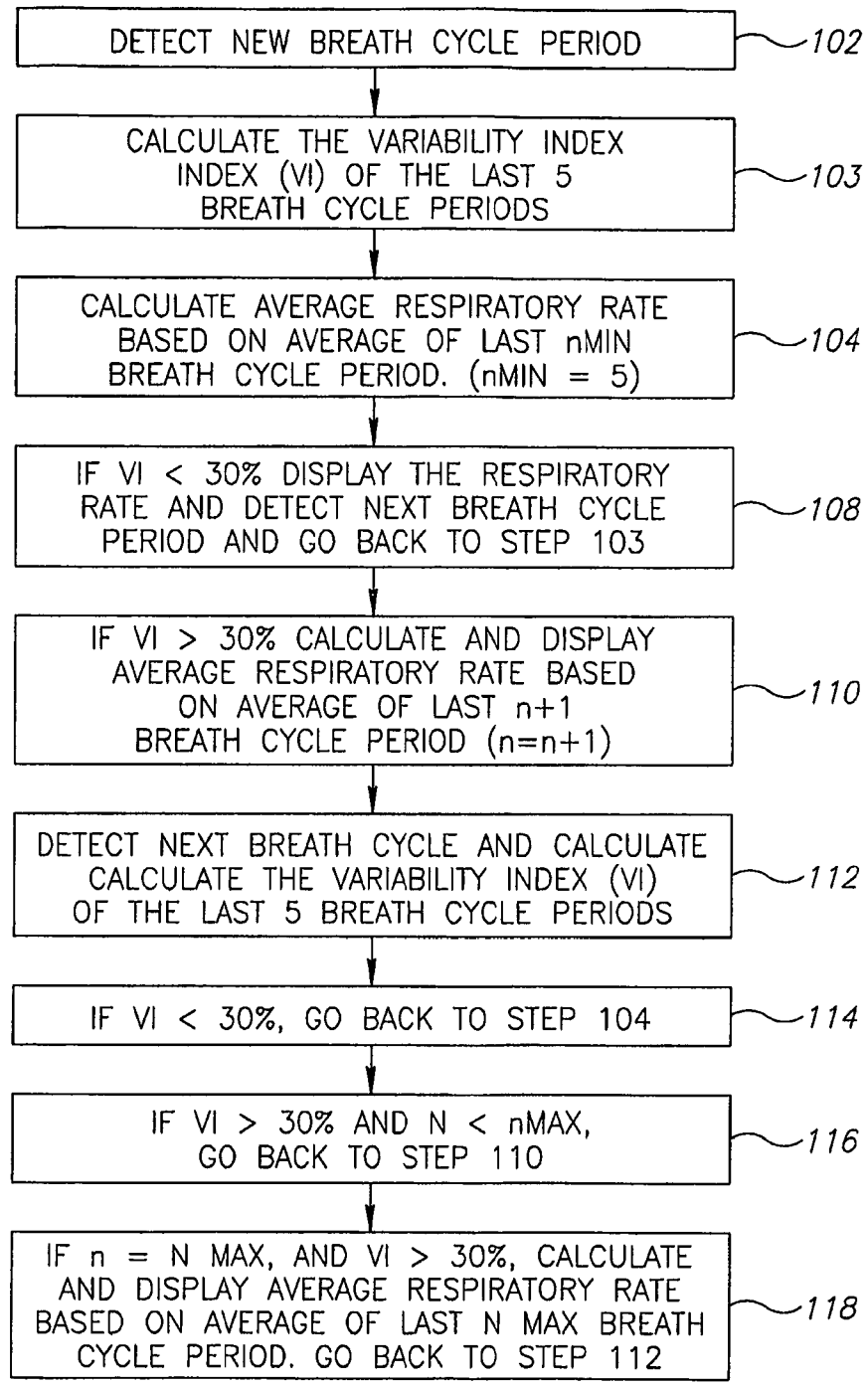
FIG. 2—a flow chart diagram of a method for averaging a breath related parameter, according to some exemplary embodiments.
Figure 3A:
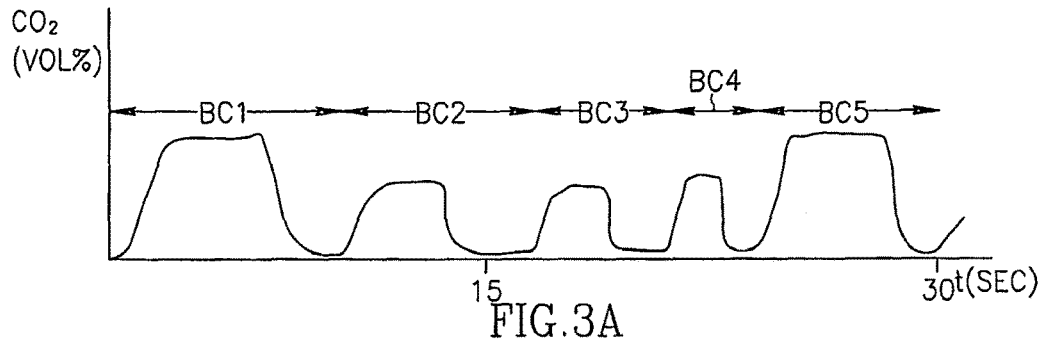
FIGS. 3A-3D—schematic exemplary graphs of breath cycle measurements, according to some embodiments.
Figure 3B:
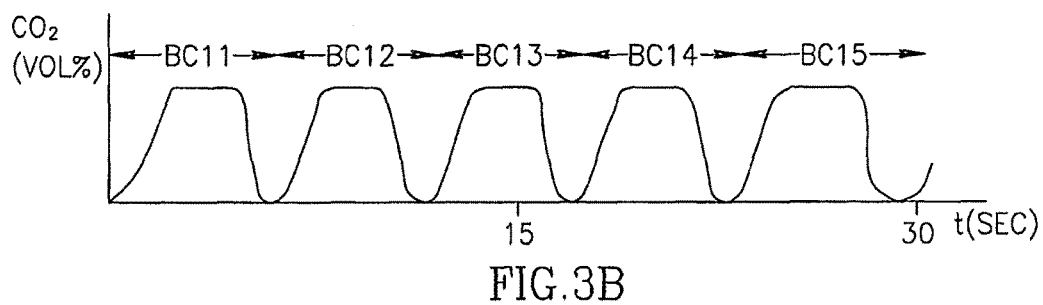
Figure 3C:
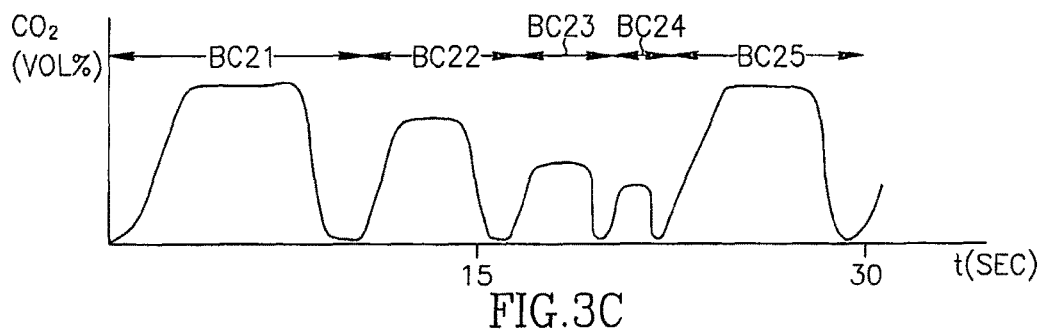
Figure 3D:
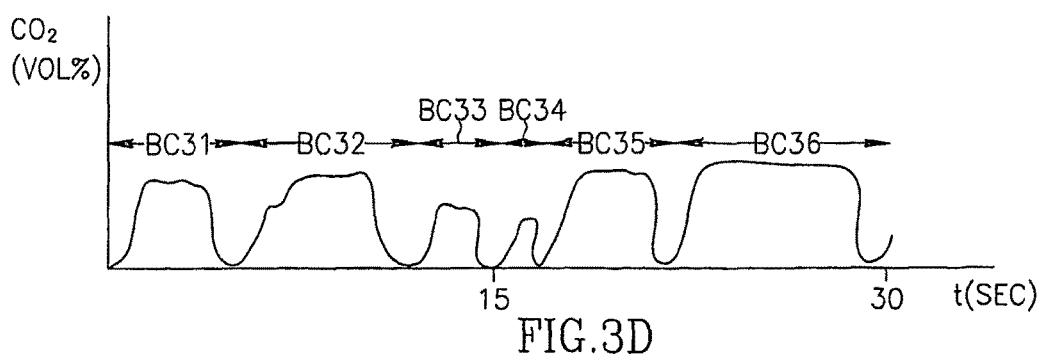

Reference is now made to FIG. 2, which illustrates a flow chart diagram of a method for averaging a breath related parameter, according to some exemplary embodiments. As shown in FIG. 2, first step 102 includes detecting a new breath cycle period. Detecting the breath cycle period may be performed in various ways, such as, for example, based on the breath cycle waveform and the given change of $CO_2$ for a given period; based on more sophisticated decision processes to determine in retrospect, when a breath cycle starts and ends; and the like, or any combination thereof. After detecting the breath cycle time period, in step 103, the variability index of the last, for example, 5 (or any other number, in the range of 2-20) breath cycle periods may also be calculated. Each time a new breath cycle period is entered, (as performed in step 102), the oldest breath cycle period (the breath cycle period that was $n_{min}+1$ (in this example, 6) cycles back), is dropped from the calculations, but remains stored in the memory so it may later be used only if in step 103 the variability index (VI) is higher than the predefined threshold, as detailed below. According to some embodiments, the variability index may be a measure of the dispersion and may be calculated by measuring the standard deviation of the breath cycle period and dividing by the mean of the breath cycle periods (for example: (Sdev/µ or $\sqrt{((\Sigma(x-\mu)^2)/N))/\mu}$). Next, as shown in step 104, the average respiratory rate may be calculated. After every new, detected breath cycle, a new respiratory rate is calculated based on the average of the last $n_{min}$ breath cycle periods. n is the number which defines how many of the last detected breath cycles are used to calculate the average, and it may range from $n_{min}$, which is the lowest value of n, to $n_{max}$, which is the highest value of n. According to some exemplary embodiments presented in FIG. 2, $n_{min}$ is 5 and $n_{max}$ is 12. In the next step, 108, the calculated variability index (VI) is compared to a predetermined threshold. For example, the threshold may be is predefined/predetermined as a high variability index. This value may be determined, for example, at about 30%. If the calculated variability index is below the threshold, the average respiratory rate calculated in step 104 is displayed. In addition, the next breath cycle period may be detected and the calculations may proceed by returning to step 103. As long as the new, updated variability index obtained in step 103 is lower then the threshold (as performed in step 108), the detection of the next breath cycle and calculations may continue by returning to step 104. If, however, the variability index is higher than the threshold (for example, above 30%), as shown in step 110, the average respiratory rate is calculated and displayed based on the last n+1 measurements, wherein now n=n+1, and the next breath cycle period is detected. For example, if, after step 103, the variability index is higher than 30%, the average may then be calculated based on the last n+1 (in this example last 6) breath cycle measurements (by using the breath cycle that is stored in the memory and was dropped when detecting the new breath cycle in stage 102). In step 112, the next breath cycle is detected and the variability index is calculated as above, based on the last 5 breath cycle periods. If the calculated variability index is lower than the threshold (such as below 30%), the calculations may proceed by returning to step 104. As shown in step 116, if the variability index is higher than the predetermined threshold (such as, for example, higher than 30%), and as long as n is lower than $n_{max}$ (for example, 12), step 110 is returned. If n equals $n_{max}$ (for example, 12), the variability index is higher than the predetermined threshold (such as, for example, higher than 30%), as in step 118, the average respiratory rate is calculated based on $n_{max}$ and displayed, and step 112 is returned. In addition, various algorithms and mathematical filters, either known today or to be developed in the future may also be implemented in the method, in any of the steps described above herein.

Reference is now made to FIG. 3, which illustrates exemplary graphs of breath cycle measurements that may be used in the method for averaging a breath related parameter. Shown in FIG. 3A is a graph, which illustrates expired $CO_2$ Vol (%, y-axis) over time (t, (seconds), x-axis) of a normal, typical breathing. As shown in the graph, over a time period of 30 seconds, 5 breath cycles (numbered as BC1, BC2, BC3, BC4 and BC5) are detected. As shown, the measured breath cycles are not identical and vary in various parameters, such as, for example: waveform patterns of the various breath cycles, level of the expired $CO_2$ (intensity level), slopes of various stages of the breath cycles, length of the various breath cycles, and the like. In the example illustrated in FIG. 3A, the calculated respiratory rate is 10 breath per minute (BPM). Shown in FIG. 3B is a graph, which illustrates expired $CO_2$ Vol (%, y-axis) over time (t, (seconds), x-axis). As shown in the graph, over a time period of 30 seconds, 5 breath cycles (numbered as BC1, BC12, BC13, BC14 and BC15) are detected. As shown in the graphs, the five breath cycles are similar; the time period of each breath cycle is 6 seconds and hence the average time period of the breath cycle is 6 seconds. The calculated level of dispersion, which may calculated according to the formula detailed above herein (Sdev/µ), over the last detected 5 breath cycles is 0%. Therefore, since the dispersion level is low (below a threshold, of, for example, 30%) the averaging time may remain unchanged and stay at, for example, a minimum time period of 30 seconds. Shown in FIG. 3C is a graph, which illustrates expired $CO_2$ Vol (%, y-axis) over time (t, (seconds), x-axis). As shown in the graph, over a time period of 30 seconds, 5 breath cycles (numbered as BC21, BC22, BC23, BC24 and BC25) are detected. As shown in the exemplary graphs, the five breath cycles are not identical and the time period of breath cycles is 10, 6, 4, 2, 8, seconds, respectively. The average time period of BC20, BC21, BC22, BC23 and BC24 breath cycle is 6 seconds. The calculated level of dispersion, which may be calculated according to the formula detailed above herein (Sdev/µ), over the last detected 5 breath cycles is 20%. Therefore, since the dispersion level is low (below a threshold, of, for example, 30%) the averaging time may remain unchanged and stay at, for example 30 seconds. Shown in FIG. 3D is a graph, which illustrates expired $CO_2$ Vol (%, y-axis) over time (t, (seconds), x-axis). As shown in the graph, over a time period of 30 seconds, 6 breath cycles (numbered as BC31, BC32, BC33, BC34, BC35 and BC36) are detected. The breath cycles are not identical and vary in various ways, such as, for example, the waveform pattern of the various breath cycles, the intensity levels, length of the breath cycles, and the like. For example, regarding the length period of the breath cycles, the measured length period of BC30, BC31, BC32, BC33, BC34 and BC35 breath cycles are 5, 9, 3, 4, 5 and 12 seconds, respectively. The calculated level of dispersion, which may be calculated according to the formula detailed above herein (Sdev/µ), over the last detected 5 breath cycles is 55%. Thereof, since the dispersion level is high (above a threshold, of, for example, 30%) the averaging time may be increased to, for example 60 seconds.

According to some embodiments, the breath related parameter may include the $CO_2$ waveform pattern. $CO_2$ waveforms, such as the exemplary waveforms depicted in FIG. 1 may display various patterns under various physical conditions. Moreover, various parts/regions of the waveform (for example, stages I, II, III, IV in FIG. 1) may be indicative of a physiological condition. The $CO_2$ waveform pattern may include various characteristics, such as, for example, the slopes of the various stages of the changes of $CO_2$ levels, the integral area defined by the various stages, the amplitude (intensity level) of the $CO_2$ levels in various stages of the $CO_2$ levels, and the like, or any combination thereof, that may be measured and averaged over time, to create an average pattern. The average pattern may further be used as the breath related parameter, and the breath related value may include, for example, but not limited to, the variance of the $CO_2$ waveform pattern, the standard deviation of the $CO_2$ waveform pattern, the dispersion of the $CO_2$ waveform pattern, and the like, or any combination thereof.

According to some embodiments, the breath related parameter may include a pulmonary index. The pulmonary index may include an index, which may be indicative of the physical condition of the patient, with regard to the pulmonary and/or cardiac and/or respiratory condition. The pulmonary index may be an integrated value that may be computed based on an average of an output of at least one sensor, wherein the sensors may include, such sensors as a capnograph, pulse oximeter, heart rate monitor, or any combination thereof that may be used to sense/measure various parameters, such as, for example, respiration rate, $EtCO_2$, $SpO_2$, heart rate, or any combination thereof. The pulmonary index value significance may be determined by correlating the output value of the sensor and the ordinary level of a medical condition. For example, an increase in the index value may be indicative of an improvement in the patient's condition, and a decrease in the index value may be indicative of a deterioration of a patient's condition. Hence, according to some embodiments, the pulmonary index may be used as the breath related parameter. The pulmonary index may be averaged over time, and the breath related values may include, for example, but not limited to, the variance of the pulmonary index value, the standard deviation of the pulmonary index value, the pulmonary index value, the variance of the breath cycle, and the like, or any combination thereof.

According to some embodiments, there is further provided a method for measuring a breath related parameter, such as but not limited to, respiratory rate, the method includes measuring the breath related parameter over a first period of time, wherein the result of the measurement is averaged over the first period of time; and predicting an average result of the breath related parameter that would be obtained if the breath related parameter was measured over a second period of time, wherein, for example, the first period of time is shorter than the second period of time.

As mentioned above, if the averaging over a longer period of time can indicate and verify how real a medical event truly is, there may be other parameters, that if measured may predict in a far shorter period what the average would reach if left to average over a longer time period. Hence it may be possible to predict within, for example, 30 seconds with a high degree of accuracy what the average will be after being measured for two minutes. One such measure is the measure of stability.

The methods referred to herein may also include setting off an alarm if the average value is above or below a predefined (and optionally adjustable) threshold.

According to some embodiments, the limit ranges of the breath related parameters, such as, for example, the respiratory rate, may be adjusted to fit the individual breath characteristics of the patient being monitored. For example, for newborns, the lower BPM threshold limits may be below 40. For infants, the lower threshold limits may be below 30. For preschool children the lower BPM threshold limits may be below 15. For children the lower BPM threshold limits may be below 10. For adults the lower BPM threshold limits may be below 4.

According to some embodiments, the methods referred to herein may include a capnographic method for measuring breath related parameters such as, but not limited to respiratory rate, $CO_2$ concentration in the ventilated breath, $EtCO_2$, and the like, or any combination thereof. The capnographic method may also be used to obtain breath related values, such as, but not limited to characteristics of individual breath cycle, for example: breath cycle standard deviation, breath cycle variance, breath cycle dispersion, waveform shape, slopes, area, waveform pattern, respiration rate, or any combination thereof.

Device

Breath monitoring devices, such as a capnograph, are generally used to monitor, in real-time, $CO_2$ concentration in a subject's ventilation and hence, among other things, to track respiratory rate.

There is provided, according to some embodiments, a capnography device including a sampler, adapted to measure a breath related parameter (such as respiratory rate) over a predetermined period of time, and a processor adapted to average the result of the measurement over the predetermined period of time.

According to some embodiments, there is further provided a capnography device including a sampler adapted to measure a breath related parameter over a predetermined period of time, a processor adapted to average the result of the measurement over the predetermined period of time, and a controller adapted to change the period of time according to the result of the measurement of the breath related parameter.

According to some embodiments, there is further provided a capnography device, including a sampler adapted to measure a breath related parameter over a predetermined period of time, a processor adapted to average the result of the measurement over the predetermined period of time, and a controller adapted to change the period of time according to the result of the measurement of the breath related parameter.

The device may be further equipped with an alert setting that may be programmed to set off an alarm when a threshold limit of various measured parameters is reached.

The threshold limit may include a range of values. In addition, the device may be further equipped with analyzers and controllers used to automatically analyze and calculate, in real-time various parameters, based upon measurements and data input. The parameters may include for example respiratory rate, averaging time, alarm threshold limits, breath cycles related parameters, measurements time, or any combination thereof. The device may use any of the methods described above for the various calculations.

According to some embodiments, the period used by the device for measurements/calculations may be a time period (such as for example, number of seconds) or a time period determined by number of occurrences of events, such as for example, number of breath cycles.

According to some exemplary embodiments, the device may calculate in real-time, respiratory rate by measuring the number of breaths over any time period in the length of between 15 seconds up to 2 minutes and the BPM would then be averaged accordingly. The average BPM may be calculated by multiplying or dividing the measurements by the measured time period, so that the rate would display breath numbers per minute. The time period may be determined by the user or may be automatically set by the device, according to measurements and data input. For example, the device may calculate respiratory rate by measuring the number of breaths over 30 seconds, and the average BPM would then be calculated by multiplying the number of measured breaths by 2, so that the number of breaths per minute is obtained. For example, the device may calculate respiratory rate by measuring the number of breaths over a time period of 120 seconds, and the average BPM would then be calculated by multiplying the number of measured breaths by 0.5, so that the number of breaths per minute is obtained.

According to some embodiments, the device may be further equipped with an analyzer that may utilize a more sophisticated and complex algorithms used to calculate, in real time, the average respiratory rate. The algorithm used by the analyzer is such that the averaged breath related parameter is not calculated as a simple average, but rather different levels of weighting may be given to various parameter characteristics (such as temporal characteristics) during the measurements. For example, in determining the averaged BPM, different levels of weighting are given to different breaths during the measurements, such as for example; the last N numbers of breaths are given different levels of weighting when average is calculated. N may be any number of between 2 to 18.

According to some embodiments, the device analyzer may utilize an algorithm that may be used to calculate the average BPM by measuring number of breaths over a time period in the range of from about 15 seconds to 2 minutes, wherein the last N number of breaths is given a higher level of weighting when the average is calculated. N may be any number of breaths in the range of from 2 to 18. For example, the device analyzer may utilize an algorithm that may be used to calculate the average BPM by measuring the number of breaths over a time period of 120 seconds, wherein the last 3 breaths are given a higher level of weighting when the average is calculated.

According to some embodiments, the device analyzer may utilize an algorithm that may be used to calculate the average BPM by measuring number of breaths over a time period in the range of from about 15 seconds to 2 minutes, wherein the first N number of breaths is given a higher level of weighting when the average is calculated. N may be any number of breaths in the range of from 2 to 18. For example, the device analyzer may utilize an algorithm that may be used to calculate the average BPM by measuring breath number over a time period of 120 seconds, wherein the first 3 breaths are given a higher level of weighting when the average is calculated.

According to some embodiments, the device analyzer may utilize an algorithm that may be used to calculate the average BPM by measuring number of breaths over a time period in the range of from about 15 seconds to 2 minutes, wherein the first N number of breaths and the last N number of breaths are given a higher level of weighting when the average is calculated. N may be any number of breaths in the range of from 2 to 18. For example, the device analyzer may utilize an algorithm that may be used to calculate the average BPM by measuring number of breaths over a time period of 120 seconds, wherein the first 3 breaths and the last 3 breaths are given a higher level of weighting when the average is calculated.

According to some embodiments, the device analyzer may utilize an algorithm that may be used to calculate the average BPM by measuring number of breaths over a time period in the range of from about 15 seconds to 2 minutes, wherein the N number of breaths that are between the first N1 breaths and the last N2 breaths are given a higher level of weighting when the average is calculated. N may be any number of breaths in the range of from 2 to 17. N1 and N2 may be any number of breaths in the range of from 1 to 18. For example, the device analyzer may utilize an algorithm that may be used to calculate the average BPM by measuring number of breaths over a time period of 120 seconds, wherein the breaths that are between the first 2 breaths and the last 2 breaths are given a higher level of weighting when the average is calculated.

According to some embodiments, the device analyzer may utilize an algorithm that may be used to calculate the average BPM by measuring number of breaths over a time period in the range of from about 15 seconds to 2 minutes. If the measured breath rate is higher than Y1, the last N number of breaths are given a higher level of weighting. If the measured breath rate is lower than Y2, the first N number of breaths are given a higher level of weighting when the average is calculated. N may be any number of breaths in the range of from 2 to 18. Y1 may be any number higher than 10. Y2 may be any number lower than 10. For example, the device analyzer may utilize an algorithm that may be used to calculate the average BPM by measuring number of breaths over 120 seconds. If the measured respiratory rate is higher than 12, the last 3 breaths are given a higher level of weighting when the average is calculated. If the measured respiratory rate is lower than 8, the first 3 breaths are given a higher level of weighting when the average is calculated.

According to other embodiments, the device may further include a controller that may be adapted to incorporate a breath related value that may be related to the breath related parameter being monitored. The breath related value may be indicative of the reliability, trustworthiness and consistency of the breath related parameter being measured. The breath related value may then be used to dictate in real-time the level of averaging and/or the time period used for calculating the average of the breath related parameter being monitored. If the breath related value indicates, for example, inconsistency, then the averaging time, or time period used for calculating the breath related parameter (such as for example, respiratory rate) may be increased. On the other hand if there is strong consistency, the averaging time, or time period used for calculating the breath related parameter (such as for example, respiratory rate), may be reduced to a minimum value.

According to some embodiments, the breath related value may be obtained from a direct measurement of breath related parameters, or may be obtained indirectly from measurements of various breath related parameters. The breath related value may be analyzed by the device and may include, for example, values such as standard deviations, variance, dispersion, slopes, and the like, of the data or any other measured or calculated parameters that may indicate consistency and stable trends, or oppositely, indicate inconsistency.

According to some embodiments, the device may analyze the breath related values over a time period in the range of from 5 seconds to 3 minutes that may be in parallel with the time period over which the breath related parameter is measured. The device may analyze the breath related values that were taken over a time period in the range of from 5 seconds to 3 minutes prior to the measurement of the breath related parameter. The device may analyze the breath related values over a time period that is determined according to number of occurrences of events.

According to further embodiments, the device may be further equipped with a digital memory that may store the breath related values taken over a time period of 5 seconds to 3 minutes (or a time period determined by 2-20 breath cycles) in parallel with the measurement of the breath related parameter measurements. For example, the digital memory may store data regarding such values as breath cycle slopes, breath cycle standard deviation, breath cycle variance, and breath cycle dispersion, collected over a time period that is parallel with the measurement of the respiratory rate.

According to further embodiments, the device may be further equipped with a digital memory that may store the breath related values taken over a time period of 5 seconds to 3 minutes (or a time period determined by 2-20 breath cycles) prior to the measurement of the breath related parameter. For example, the digital memory may store data regarding values such as breath cycle slopes, breath cycle standard deviation, breath cycle variance, and breath cycle dispersion, collected over a time period of 5 seconds to 3 minutes prior to the measurement of the respiratory rate.

According to further embodiments, the device digital memory may also be adapted to be updated with new parameters and to purge older parameters as the measurement progresses over time, so that the device may accommodate and analyze new measured data and input variables.

According to further embodiments, the device may include a controller that may be adapted to intermittently calculate breath related parameters and values based on data stored in the digital memory. The controller may further be adapted to calculate an adaptive time window, wherein the breath related value may be used to control the extent of averaging, and/or the time period for calculation of the breath related parameter being monitored. Hence, the device may automatically determine the averaging time or the time period needed for calculation of the breath related parameter being monitored, by continuously analyzing the measured data and variables, such as the breath related values. This way, the number of non-clinically significant alarms may be considerably reduced without the need to "artificially" increase averaging periods or provide more extreme alarm limits, which may waste valuable time before a health care provider will react to the event.

According to some embodiments, the device controller may be further adapted to determine how close the breath related parameter is to the defined alarm limits, and so when the breath related parameter being measured is reaching close to the limits, averaging time may be changed accordingly.

According to some exemplary embodiments, if the respiratory rate is the breath related parameter being monitored, any number of seconds in the range of 15-120 seconds may be used for calculating the average respiratory rate. The breath related value may be obtained from measurements taken in parallel with the measurement of the respiratory rate, over a time period of 15-120 seconds. Alternatively, the breath related value may be obtained from measurements taken over any number of seconds in the range of 5-360, prior to the measurements of the respiratory rate. If the breath related value deviates from predetermined limits, then the period for calculating the breath rate is changed accordingly to accommodate the new condition.

According to some exemplary embodiments, if the respiratory rate is the breath related parameter being monitored, any time period that is determined by number of breath cycles in the range of 2-20 may be used for calculating the average respiratory rate. The breath related value may be obtained from measurements taken in parallel with the measurement of the respiratory rate. Alternatively, the breath related value may be obtained from measurements taken over any time period determined by the number of breath cycles in the range of 2-20, prior to the measurements of the respiratory rate. If the breath related value deviates from predetermined limits then the period for calculating the breath rate is changed accordingly to accommodate the new condition.

According to some embodiments, the device may be programmed to set off an alarm when the respiratory rate, calculated by any of the method described is outside the ranges of predetermined threshold limit. The alarm threshold limits may be determined by the user or may also be automatically determined by the device, according to the data measurements and the variables input. The threshold limits may also be determined according to individual breath characteristic of the patient being monitored, such as for example: newborns (lower threshold limit of below 40 BPM), infants (lower threshold limit of below 30 BPM), preschool children (lower threshold limit of below 15 BPM), children (lower threshold limits of below 10 BPM). For adults, the alarm lower threshold limits may be any number in the range of 4 to 20 BPM, and when the respiratory rate is lower than the threshold limit, an alarm may be set off.

According to some exemplary preferred embodiments, the threshold may be determined at 6 BPM. The threshold may be 8 BPM; the threshold may be 10 BPM; the threshold may be 12 BPM.

According to some embodiments, the device may further include a monitor displaying the breath related parameters being measured, as well as the breath related values according to which the averaging time and alarm limits are calculated and determined. The monitor may further display any parameter useful for the health care provider in tracking the patient's breath and medical condition. Such parameters may include, for example, alarm threshold limits, breath-averaging time, period length (time/number of breaths) over which the average was determined, which breaths were weighted during the measurements period and the average determination. The displaying monitor of the device may be integrally formed with the device. The displaying monitor be may functionally connected to the device. The visual display may be presented in the form of a graphic presentation, numerical presentation or any combination thereof. Such a visual display is important for the health care provider to track the averaging time, alarm limits and measured parameters that were used for the calculation, so that the level of reliability/consistency of the real-time measurements may be assessed.

While a number of exemplary aspects and embodiments have been discussed above, those of skill in the art will recognize certain modifications, permutations, additions and sub-combinations thereof. It is therefore intended that the following appended claims and claims hereafter introduced be interpreted to include all such modifications, permutations, additions and sub-combinations as are within their true spirit and scope.

EXAMPLES

Example 1

Several clinical trials performed on several hundreds of patients in a pain management environment have clearly shown the reality that increasing averaging time reduces false (non-clinically significant) alarms. This is also proven for reducing alarm thresholds (for low limit alarms and vice versa for high limit alarms). However, increasing averaging times and said periods, together with reduced alarm limits, may save annoying false alarms but promotes late reactions to important events. Table 1 summarizes test results from such a study:

TABLE 1

Number of non-clinically significant alarms as a function of alarm threshold limit and averaging time.

| Alarm Limit (BPM)\ Average time (sec.) | 30 | 60 | 90 | 120 |
|---|---|---|---|---|
| 6 | 121 | 39 | 18 | 9 |
| 8 | 325 | 156 | 74 | 41 |
| 10 | 531 | 301 | 172 | 122 |
| 12 | 848 | 470 | 260 | 188 |

Example 2

Several clinical trials performed on several hundreds of patients in sleep labs have clearly shown the reality that increasing averaging time reduces false (non-clinically significant) alarms. This is also proven for reducing alarm thresholds (for low limit alarms and vice versa for high limit alarms). Table 2 summarizes test results from such a study:

TABLE 2

Number of non-clinically significant alarms as a function of alarm threshold limit and averaging time.

| Alarm Limit (BPM)\ Average time (sec.) | 30 | 60 | 90 | 120 |
|---|---|---|---|---|
| 6 | 684 | 254 | 155 | 105 |
| 8 | 1186 | 572 | 318 | 208 |
| 10 | 1821 | 921 | 518 | — |
| 12 | 2852 | 1627 | 938 | — |

Example 3

Sample Calculations of Breath Related Values 3.1. Calculation of Breath Cycle Variance and Breath Cycle Dispersion:

Respiratory rate is measured over a time period of 30 seconds. During the 30 seconds, three breath cycles are measured and timed as 12, 8 and 10 seconds long. According to the formula described above herein, the variance will equal:

$$\sigma^2 = (\Sigma(x-\mu)^2)/N = ((12-10)^2 + (8-10)^2 + (10-10)^2)/3 = 2.666.$$

(Since this is the entire population, the formula used is slightly different from that used when having only a sample). In order to obtain the dispersion value according to these calculations, the variance is divided by the mean, that is $\sigma^2/\mu = 2.666/10 = 26.6\%$. The 26.6% may now be used as a level of dispersion for that group of breath cycles measured. A high value will define high dispersion. For example, if we predefine that we only display a new, updated value of the respiratory rate when the dispersion is lower than 25%, in this example, the result is outside the range; hence we have to continue gathering more data:

If, for example, the next cycle is 11 seconds, then: The new calculated variance value is: $\sigma^2 = (\Sigma(x-\mu)^2)/N = ((12-10.25)^2 + (8-10.25)^2 + (10-10.25)^2 + (11-10.25)/4 = 2.187$, and the dispersion is $\sigma^2/p = 2.187/10.25 = 21.3\%$. (The mean changed to 10.25 after the fourth cycle is included in the calculations). Since the result, 21.3%, is lower than the predetermined limit of 25%, the new, updated respiratory rate value: 10.25/60=5.8 BPM (or rounded as 6 BPM) is displayed.

3.2. Calculation of Breath Cycle Standard Deviation and Breath Cycle Dispersion:

Respiratory rate is measured over a time period of 30 seconds. During the 30 seconds, three breath cycles are measured and timed as 12, 8 and 10 seconds long. According to the formula described above herein, the variance will equal:

$$\sigma^2 = (\Sigma(x-\mu)^2)/N = ((12-10)^2 + (8-10)^2 + (10-10)^2)/3 = 2.666$$

and the standard deviation (Sdev.) will thus equal the Square Root of $\sigma^2 (\sqrt{2.666}) = 1.632$. The dispersion value according to this calculation is: $Sdev/\mu = 1.632/10 = 16.3\%$.

The 16.3% may now be used as a level of dispersion for that group of breath cycles measured. A high value will define high dispersion. For example, if we predefine that we only display a new, updated value of the respiratory rate when the dispersion is lower than 15%, in this example, the result is outside the range; hence we have to continue gathering more data:

If, for example, the next cycle is 11 seconds, then: the new calculated variance value is: $\sigma^2 = (\Sigma(x-\mu)^2)/N = ((12-10.25)^2 + (8-10.25)^2 + (10-10.25)^2 + (11-10.25)/4 = 2.187$; the standard deviation would be: $Sdev. = $ Square Root of $\sigma^2 (\sqrt{2.187}) = 1.47$; and the dispersion would be: $Sdev/\mu = 1.47/10.25 = 14.4\%$. Since the result, 14.4%, is lower than the predetermined limit of 15%, the new, updated respiratory rate value: 10.25/60=5.8 BPM (or rounded as 6 BPM) is displayed.

What we claim is:

1. A method for determining an average breath related parameter over an adaptable period of time, the method comprising:

measuring a plurality of breath related parameters of a patient over time using a capnograph; and using a processor to:
  receive the plurality of breath related parameters;
  determine a plurality of breath cycle periods based on a change in at least one breath related parameter of the plurality of breath related parameters over the period of time; and
  for each breath cycle period of the plurality of breath cycle periods determined over the period of time:
    calculate a variability index of the at least one breath related parameter of the plurality of breath related parameters in the last detected n breath cycle periods over the period of time, wherein n is at least 2;
    determine an average of the at least one breath related parameters of the plurality of breath related parameters in the n breath cycle periods;
    adjust the period of time to include n+1 breath cycle periods after averaging the at least one breath related parameter when the variability index is above a predetermined variability index threshold and recalculate the average of the at least one breath related parameter based on the plurality of breath related parameters in the n+1 breath cycle periods; and
    output an alarm associated with a physical condition of the patient when the average breath related parameter is outside a predetermined parameter threshold.

2. The method of claim 1, wherein the plurality of breath related parameters comprises a $CO_2$ waveform, end-tidal ($EtCO_2$), a variance in a pulmonary index, a standard deviation of the pulmonary index, or any combinations thereof.

3. The method of claim 1, wherein the variability index is determined based on a standard deviation of the breath cycle period and a mean of the n breath cycle periods.

4. The method of claim 1, wherein the variability index is a measure of dispersion.

5. The method of claim 1, comprising displaying the average breath related parameter when the variability index is outside the predetermined variability index threshold for a predetermined period of time.

6. The method of claim 5, wherein the predetermined period of time is between 15 and 120 seconds.

7. A medical monitoring system comprising:
a capnograph comprising a carbon dioxide ($CO_2$) sensor configured to measure a plurality of breath related parameters of a patient over a period of time; and a processor configured to:
receive the plurality of breath related parameters;
determine a plurality of breath cycle periods based on a change in at least one breath related parameter of the plurality of breath related parameters over the period of time; and
  for each breath cycle period of the plurality of breath cycle periods determined over the period of time:
    calculate a variability index of the at least one breath related parameter of the plurality of n breath related parameters in the most recently detected n breath cycle periods over the period of time, wherein n is at least 2;
    determine an average of the at least one breath related parameter of the plurality of breath related parameters in the n breath cycle periods;
    adjust the period of time to include n+1 breath cycle periods after averaging the at least one breath related parameter when the variability index is above a predetermined variability index threshold and recalculate the average of the at least one breath related parameter based on the plurality of breath related parameters in the n+1 breath cycle periods; and
    output an alarm associated with a physical condition of the patient when the average breath related parameter is outside a predetermined parameter threshold.

8. The medical monitoring system of claim 7, wherein the plurality of breath related parameters comprises a $CO_2$ waveform, end-tidal $CO_2$ (Et $CO_2$), a variance in a pulmonary index, a standard deviation of the pulmonary index, or any combinations thereof.

9. The medical monitoring system of claim 7, wherein the variability index is a measure of dispersion, and wherein the processor is configured to determine the variability index based on a standard deviation of the breath cycle period and a mean of the n breath cycle periods.

10. The medical monitoring system of claim 7, wherein the processor is configured to determine the breath cycle period based on a waveform of the at least one breath related parameters.

11. The medical monitoring system of claim 7, wherein the average breath related parameter is a weighted average of the plurality of breath related parameters.

12. The medical monitoring system of claim 7, comprising a display configured to display the average breath related parameter when the variability index is within the predetermined variability index threshold.

13. The medical monitoring system of claim 7, comprising a display configured to display the average breath related parameter when the variability index is outside the predetermined variability index threshold for a predetermined period of time.

14. The medical monitoring system of claim 13, wherein the predetermined period of time is between 15 and 120 seconds.

15. The medical monitoring system of claim 7, further comprising a pulse oximeter, a heart rate monitor, or both.

16. A medical monitoring system, comprising:
a capnograph configured to measure a plurality of breath related parameters of a patient over a period of time; and
a processor configured to:
  determine a plurality of breath cycle periods based on a change in at least one breath related parameter of the plurality of breath related parameters over the period of time; and
  for each breath cycle period of the plurality of breath cycle periods:
    calculate a variance, a standard deviation, or a variability index for data associated with the at least one breath related parameter measured for n breath cycle periods, wherein n is at least 2;
    determine an average of the at least one breath related parameter based on the measured plurality of breath related parameters during the most recently detected n breath cycle periods;
    compare the variance, the standard deviation, or the variability index to a predetermined threshold after averaging the at least one breath related parameter;
    adjust the period of time to include n+1 breath cycle periods when the variance, the standard deviation, or the variability index is above a predetermined threshold;
    recalculate the average of the at least one breath related parameter based on the measured plurality of breath related parameters during the n+1 breath cycle periods; and display the average breath related parameter on a display communicatively coupled to the capnograph.

17. The medical monitoring system of claim 16, wherein the processor is configured to output an alarm associated with a physical condition of the patient when the average breath related parameter is outside a predetermined threshold.

18. The medical monitoring system of claim 16, wherein the processor is configured to display the average breath related parameter in response to the variability index being outside the predetermined threshold after a predetermined period of time.

19. The medical monitoring system of claim 16, wherein the plurality of breath related parameters comprises a respiratory rate, a $CO_2$ waveform, end-tidal $CO_2$ ($EtCO_2$), a variance in a pulmonary index, a standard deviation of the pulmonary index, or any combinations thereof.

20. The medical monitoring system of claim 16, comprising a pulse oximeter, a heart rate monitor, or both.

* * * * *